United States Patent
Hoffman et al.

(10) Patent No.: US 8,308,774 B2
(45) Date of Patent: Nov. 13, 2012

(54) SPINAL ROD REDUCER AND CAP INSERTION APPARATUS

(75) Inventors: Jeffrey Hoffman, Marquette, MI (US); Maria M. Norman, Negaunee, MI (US); Scott J. Parrow, Ishpeming, MI (US); Michael D. Ensign, Salt Lake City, UT (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 899 days.

(21) Appl. No.: 12/031,655

(22) Filed: Feb. 14, 2008

(65) Prior Publication Data

US 2009/0157125 A1    Jun. 18, 2009

Related U.S. Application Data

(60) Provisional application No. 60/901,157, filed on Feb. 14, 2007, provisional application No. 61/024,505, filed on Jan. 29, 2008.

(51) Int. Cl.
*A61B 17/88* (2006.01)

(52) U.S. Cl. ..................... 606/279; 606/86 A

(58) Field of Classification Search ............. 606/279, 606/86 A
See application file for complete search history.

(56) References Cited

U.S. PATENT DOCUMENTS

| | | | |
|---|---|---|---|
| 1,359,164 A | 11/1920 | Giudice | |
| 1,832,879 A | 11/1931 | Ruskin | |
| 1,863,037 A | 6/1932 | Archbold | |
| 1,977,282 A | 10/1934 | Kruse | |
| 1,985,108 A | 12/1934 | Rush | |
| 2,370,308 A | 2/1945 | Hanson | |
| 2,523,385 A | 9/1950 | Mead | |
| 2,594,102 A | 4/1952 | Vollmer | |
| 2,598,650 A | 5/1952 | Smith et al. | |
| 2,655,953 A | 10/1953 | Miloche | |
| 2,664,774 A | 1/1954 | Harvie | |
| 2,669,145 A | 2/1954 | Mead | |
| 2,814,222 A | 11/1957 | Sanders | |
| 3,181,181 A | 5/1965 | Buckley et al. | |
| 3,477,429 A | 11/1969 | Sampson | |
| 3,486,505 A | 12/1969 | Morrison | |
| 3,618,612 A | 11/1971 | Ahn | |
| 3,641,652 A | 2/1972 | Arnold et al. | |
| 3,981,308 A | 9/1976 | Schlein | |

(Continued)

FOREIGN PATENT DOCUMENTS

WO      9311715      6/1993

(Continued)

OTHER PUBLICATIONS

Brochure, "Spiral Radium 90D™ Surgical Technique," Tyco Healthcare/Surgical Dynamics, 11 pages.

(Continued)

*Primary Examiner* — Ellen C Hammond
(74) *Attorney, Agent, or Firm* — Fitch, Even, Tabin & Flannery, LLP

(57) ABSTRACT

A medical instrument apparatus and method is provided for positioning and securing a spinal rod to a coupling device anchored to a vertebra. A reducer assembly shifts the spinal rod into place within the coupling device and a cap inserter assembly shifts a cap member into locking engagement with the coupling device to secure the spinal rod therein.

18 Claims, 33 Drawing Sheets

U.S. PATENT DOCUMENTS

| | | | |
|---|---|---|---|
| 4,050,464 A | 9/1977 | Hall | |
| 4,111,206 A | 9/1978 | Vishnevsky et al. | |
| 4,147,167 A | 4/1979 | Hickmann et al. | |
| 4,153,321 A | 5/1979 | Pombrol | |
| 4,271,836 A | 6/1981 | Bacal et al. | |
| 4,316,468 A | 2/1982 | Klieman et al. | |
| 4,318,316 A | 3/1982 | Guilliams | |
| 4,325,376 A | 4/1982 | Klieman et al. | |
| 4,409,968 A | 10/1983 | Drummond | |
| 4,411,259 A | 10/1983 | Drummond | |
| 4,445,513 A | 5/1984 | Ulrich et al. | |
| D291,729 S | 9/1987 | Greig | |
| 4,793,225 A | 12/1988 | Berkich | |
| 4,809,695 A | 3/1989 | Gwathmey et al. | |
| 4,870,965 A | 10/1989 | Jahanger | |
| 4,896,661 A | 1/1990 | Bogert et al. | |
| 4,898,161 A | 2/1990 | Grundei | |
| 4,911,154 A | 3/1990 | Vickers | |
| 4,927,425 A | 5/1990 | Lozier | |
| 4,950,273 A | 8/1990 | Briggs | |
| 4,966,600 A | 10/1990 | Songer et al. | |
| 5,020,519 A | 6/1991 | Hayes et al. | |
| D331,625 S | 12/1992 | Price et al. | |
| 5,167,662 A | 12/1992 | Hayes et al. | |
| D346,217 S | 4/1994 | Sparker et al. | |
| 5,364,397 A | 11/1994 | Hayes et al. | |
| 5,368,596 A | 11/1994 | Burkhart | |
| 5,616,143 A | 4/1997 | Schlapfer et al. | |
| 5,704,937 A | 1/1998 | Martin | |
| 5,720,751 A * | 2/1998 | Jackson | 606/86 R |
| 5,782,831 A | 7/1998 | Sherman et al. | |
| 5,885,299 A | 3/1999 | Winslow et al. | |
| 5,899,901 A | 5/1999 | Middleton | |
| 5,910,141 A | 6/1999 | Morrison et al. | |
| 5,951,564 A | 9/1999 | Schroder et al. | |
| 6,017,342 A | 1/2000 | Rinner | |
| 6,036,692 A | 3/2000 | Burel et al. | |
| 6,063,088 A | 5/2000 | Winslow | |
| 6,083,225 A | 7/2000 | Winslow et al. | |
| 6,139,549 A | 10/2000 | Keller | |
| 6,251,111 B1 | 6/2001 | Barker et al. | |
| 6,261,296 B1 | 7/2001 | Aebi et al. | |
| 6,440,133 B1 | 8/2002 | Beale et al. | |
| 6,478,801 B1 | 11/2002 | Ralph et al. | |
| 6,648,888 B1 | 11/2003 | Shluzas | |
| 6,660,006 B2 | 12/2003 | Markworth et al. | |
| 7,828,829 B2 * | 11/2010 | Ensign | 606/305 |
| 2001/0027318 A1 | 10/2001 | Oribe et al. | |
| 2002/0026197 A1 | 2/2002 | Foley et al. | |
| 2002/0072753 A1 | 6/2002 | Cohen | |
| 2002/0095153 A1 | 7/2002 | Jones et al. | |
| 2002/0123754 A1 | 9/2002 | Holmes et al. | |
| 2002/0133157 A1 | 9/2002 | Sterett et al. | |
| 2003/0009168 A1 | 1/2003 | Beale et al. | |
| 2003/0199872 A1 | 10/2003 | Markworth et al. | |
| 2003/0225408 A1 | 12/2003 | Nichols et al. | |
| 2004/0049191 A1 | 3/2004 | Markworth et al. | |
| 2004/0147937 A1 | 7/2004 | Dunbar, Jr. et al. | |
| 2005/0277924 A1 * | 12/2005 | Roychowdhury | 606/61 |
| 2006/0025768 A1 | 2/2006 | Lott et al. | |
| 2006/0089651 A1 | 4/2006 | Trudeau et al. | |
| 2007/0093849 A1 * | 4/2007 | Jones et al. | 606/99 |
| 2007/0213722 A1 | 9/2007 | Jones et al. | |
| 2008/0154277 A1 | 6/2008 | Machalk et al. | |

FOREIGN PATENT DOCUMENTS

| | | |
|---|---|---|
| WO | 2006047659 | 5/2006 |

OTHER PUBLICATIONS

Brochure, "Universal Instrumentation (CD) for Spinal Surgery," Dr. Cotrel et al., Stuart, 1985, 20 pages.

* cited by examiner

SPINAL ROD REDUCER AND CAP INSERTION APPARATUS

RELATED INVENTION

This application claims the benefit of U.S. Provisional Application Nos. 60/901,157, filed Feb. 14, 2007, and 61/024,505 filed Jan. 29, 2008, both of which are hereby fully incorporated by reference herein.

FIELD OF THE INVENTION

This invention pertains generally to medical instruments and more specifically to spinal implant insertion instruments for spinal fixation systems.

BACKGROUND OF THE INVENTION

Various devices for internal fixation of bone segments in the human or animal body are known in the art. One type of system is a pedicle screw system, which is sometimes used as an adjunct to spinal fusion surgery, and which provides a means of gripping a spinal segment. A conventional pedicle screw system comprises a pedicle screw and a rod-receiving device. The pedicle screw includes an externally threaded stem and a head portion. The rod-receiving device couples to the head portion of the pedicle screw and receives a rod (commonly referred to as a distraction rod). Two such systems are inserted into respective vertebrae and adjusted to distract and/or stabilize a spinal column, for instance during an operation to correct a herniated disk. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

Prior art pedicle screw systems often include a top-loaded set screw compression member that is threaded into a coupling member that receives the pedicle screw and rod. It is often difficult for the surgeon to reposition or adjust the spinal rod relative to the fixation system during the surgical procedure after the compression member is inserted into the cap. Once the compression member is initially threaded into the coupling member, any space between the spinal rod and the compression member for final positioning of the rod prior to locking is randomly achieved. For example, the surgeon can randomly thread the compression member a few turns to provide a re-positioning gap between the compression member and rod or completely thread the compression member into a locking position and then back-off the threading to form this re-positioning gap. As a result, the current threaded systems for immobilizing vertebral bones with spinal rods typically require the surgeon to spend more time and guess work for achieving a gap between the compression member and rod for any final positioning of the rod prior to locking. If the re-positioning gap is not large enough, the spinal rod may bind during repositioning, thereby requiring even additional time and adjustment of the compression member to form a larger gap. All this random threading and guesswork by the surgeon requires additional time in the operating room for performing the surgical procedure on the patient.

Spinal fixation systems including locking components that only require axial shifting for locking thereof are known alternatives to utilizing rotatable threaded members. Such as axially locking spinal flexible systems are disclosed in applicants' assignees' U.S. patent application Ser. No. 11/726,868, as well as U.S. Provisional Applications Nos. 60/784,674 and 60/981,821. These systems include an anchor member (e.g., a screw or hook), a compressible inner tulip member that receives a spinal rod and a pedicle screw head snap-fit thereto, a rigid outer tulip that shifts axially over the inner tulip to compress the inner tulip tightly onto the screw head, and a cap member axially inserted between portions of the inner and outer tulip member to compress the inner tulip about the rod. This system is hereinafter referred to as the Low Top™ system, with the reservation that the instruments described herein may also be used with other spinal fixation systems with axially locking components.

SUMMARY

In accordance with the present invention, a spinal rod reducer assembly and cap inserter assembly apparatus is provided for positioning and fixation of a spinal rod, tulip assembly and cap for the Low Top™ bone fixation system. In preferred embodiments, the reducer/inserter assembly mechanically assists a surgeon in positioning a spinal rod in place over the Low Top™ inner and outer tulip members. The reducer assembly provides the surgeon the mechanical leverage to adjust the spinal rod, inner tulip member, anchor member, and vertebral bone to which the anchor member is secured into the correction position.

In the preferred form, the reducer/inserter assembly allows the spinal rod to be fully reduced into a coupling assembly prior to driving of a cap member therein for final locking of the spinal rod thereto. In this regard, the reducer assembly and the cap inserter assembly are preferably provided with a releasable coupling mechanism so that the reducer assembly can be used first for reducing the rod prior to coupling of the cap inserter assembly thereto for driving of the cap member to secure the cap to the coupling assembly. The reducer assembly has a drive release mechanism which allows the surgeon to quickly and easily slide a reducing portion of the assembly into engagement with the rod to begin the reduction procedure in which the rod is shifted or "reduced" into the tulip assembly. In another aspect of the invention, torque and counter torque handles are provided to allow application of additional force to drive the spinal rod toward and into the inner tulip member.

One advantage of the drive release mechanism is that instead of requiring a surgeon to use the torque handles of the rotary drive mechanism to shift the instrument into position, which are designed to apply a significant amount of force and therefore can take a significant amount of time to rotate, the rotary drive mechanism may be disengaged to allow the instrument to be quickly shifted into position and then re-engaged when driving force is required. Time is of the essence in spinal surgery because there is often a significant number of anchor members, tulip members, and rods that must be positioned during the limited amount of time the patient can remain under anesthetic. The reduction of surgery time correspondingly reduces the risk of infection, the risk of complications from the anesthetic itself and the recovery time of the patient. The advantage of the torque and counter torque handles is that a significant amount of force can be applied by the surgeon with this hand tool while still providing the desired direct mechanical connection and feel between the surgeon and the patient.

In one aspect, once the rod, tulip assembly, and anchor member (e.g., pedicle screw), are in position, then the Low Top™ cap can be inserted into the tulip assembly to lock all components together. The cap inserter assembly accomplishes the task of locking all the fixation system components together. The cap is first snapped into position at the distal end of the cap inserter assembly, and then inserted into a through-bore within the reducer assembly. The cap inserter assembly then locks into place within the reducer assembly. Finally, the surgeon locks the cap into place within the tulip assembly by squeezing the cap inserter handle and cap inserter actuator together to drive the cap into the assembly. Additional advantages and features of the invention will become apparent from the following description and attached claims taken in combination with the accompanying drawings.

BRIEF DESCRIPTION OF DRAWINGS

FIG. 2A is an exploded view of the reducer assembly without the inserter assembly.

DETAILED DESCRIPTION OF PREFERRED EMBODIMENTS

Figure 1:
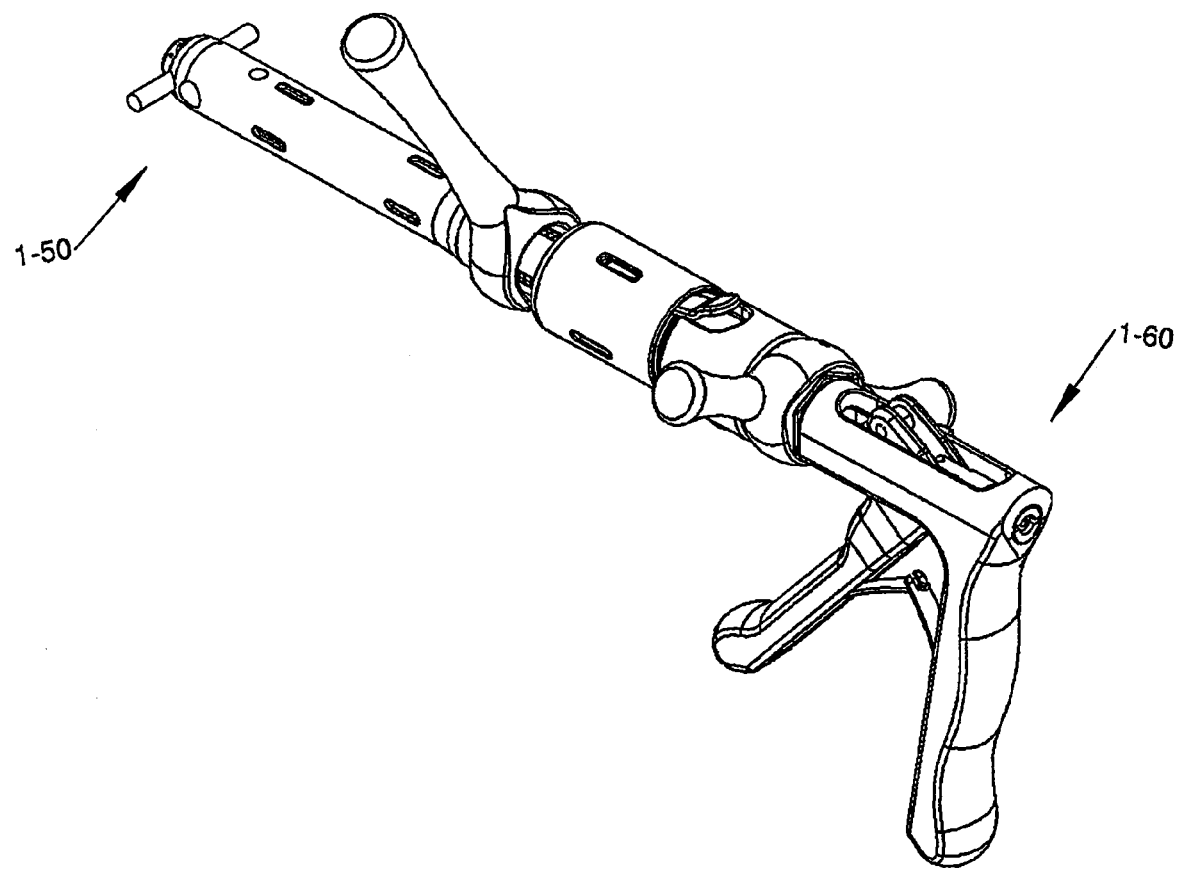
FIG. 1 is a perspective view of a reducer/inserter tool assembly showing a tool configuration in which the cap is engaged in the tulip position.

The device disclosed herein provides an insertion device for securing spinal fixation systems. In the preferred embodiment, the insertion device is similar to the class of medical instruments generally referred to as spinal rod reducers and cap inserters, but is not limited to that class of devices.

In addition to the embodiments of the Low Top™ coupling assembly or yoke assembly as described in patent application Ser. No. 11/726,868, which is hereby fully incorporated herein, the pedicle screw and yoke assembly can be cannulated, i.e. contain a pathway through the center of the insertion tool and through the entire length of the screw and assembly, so that a guide wire attached to a desired target location and threaded through the screw, assembly, and instrument to direct the system during implantation. A guide wire typically is inserted into a vertebra to achieve an initial accurate location, and the surrounding tissue is then distracted. Once the tissue is distracted, the cannulated insertion tools, cannulated pedicle screw, and yoke assembly are slid over the guide wire to the correct implantation location relative to the vertebra. The use of a guide wire with the accompanying tools may be used in minimally invasive surgeries (hereinafter MIS), which are often preferred because their accuracy reduces the amount of tissue required to be affected and reduces recovery time. In this regard, the preferred reducer/inserter apparatus described in this application would not need any alteration in design to accommodate a MIS procedure.

The following numbering convention will be used throughout all the described drawings and their descriptions. All reference numbers will begin with a number corresponding to the figure and drawing sheet number and a second number that corresponds to that particular part and corresponding reference characters. The intent of this numbering scheme is for the reader to be directed to the correct drawing and part while reading the remainder of this specification without having to guess which drawing figure to look at for the appropriate part. All parts will contain reference characters following the hyphen in the reference number that will be consistently used through all the drawings to indicate the particular part in question.

The following location and direction convention will be used throughout all the described drawings and their written descriptions. In describing the surgical instrument of the present invention, the term "proximal" refers to a direction of the instrument spaced furthest from the patient and closest the user while the term "distal" refers to a direction of the instrument spaced closest to the patient and furthest from the user. Typically, and as shown in FIG. 1, the "proximal end" of the insertion instrument 1-60 is shown on the right side of the figure near the cap inserter handle and lever. The "proximal direction" is referring to any motion toward the user and in FIG. 1 is toward the right. The "distal end" 1-50 of the insertion instrument is shown on the left side of FIG. 1 near the rod. The "distal direction" is referring to any motion toward the patient and in FIG. 1 is toward the left.

Structural and Mechanical Configuration:

Spinal fixation systems such as those described in previously-filed provisional application No. 60/981,821 (filed Oct. 29, 2007) and U.S. utility application Ser. No. 11/726,868 (filed Mar. 22, 2007), both of which are hereby fully incorporated by reference herein, can be implanted into the human body with the exemplary reducer/inserter apparatus shown in FIGS. 1 through 32.

Referring to FIG. 1, the completely assembled reducer/inserter apparatus is shown in an isometric view with the cap positioned just above the tulip. In the illustrated embodiment, the components of the reducer/inserter apparatus are cylindrical in shape to minimize the profile of the apparatus. The minimal profile of the device reduces the size of the incision necessary for surgery and subsequently assists in reducing the recovery time of the patient.

In alternative embodiments, the components can have other configurations such as hexagonal or rectangular configuration. These configurations are preferably sized to allow the shaft components of the reducer/inserter apparatus to slide axially relative to one another, such as by a telescoping type of shifting through and/or over one another.

Figure 2:
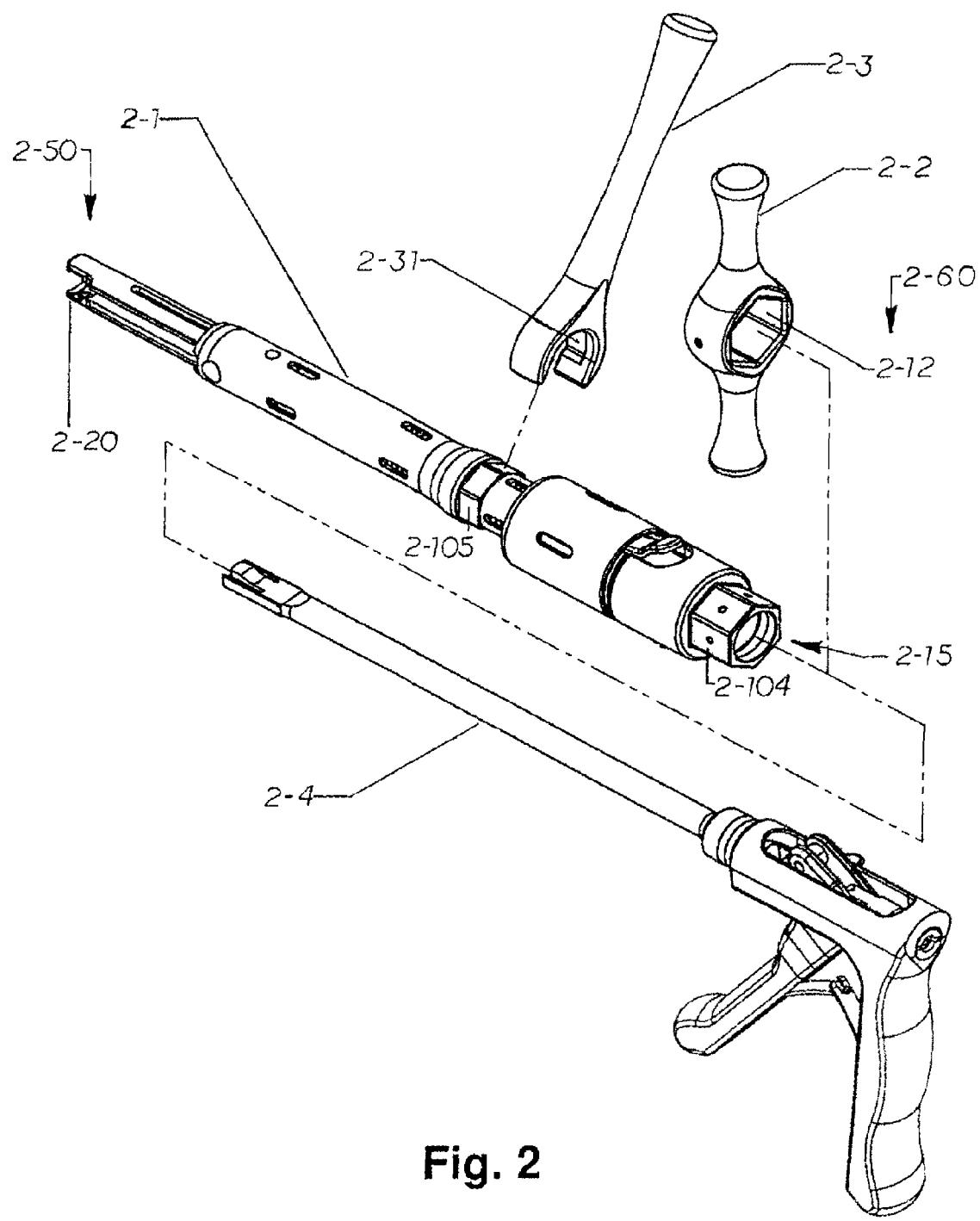
FIG. 2 is an exploded perspective view of the reducer/inserter tool assembly showing the reducer assembly cap inserter, and torque handles.
Figure 2:
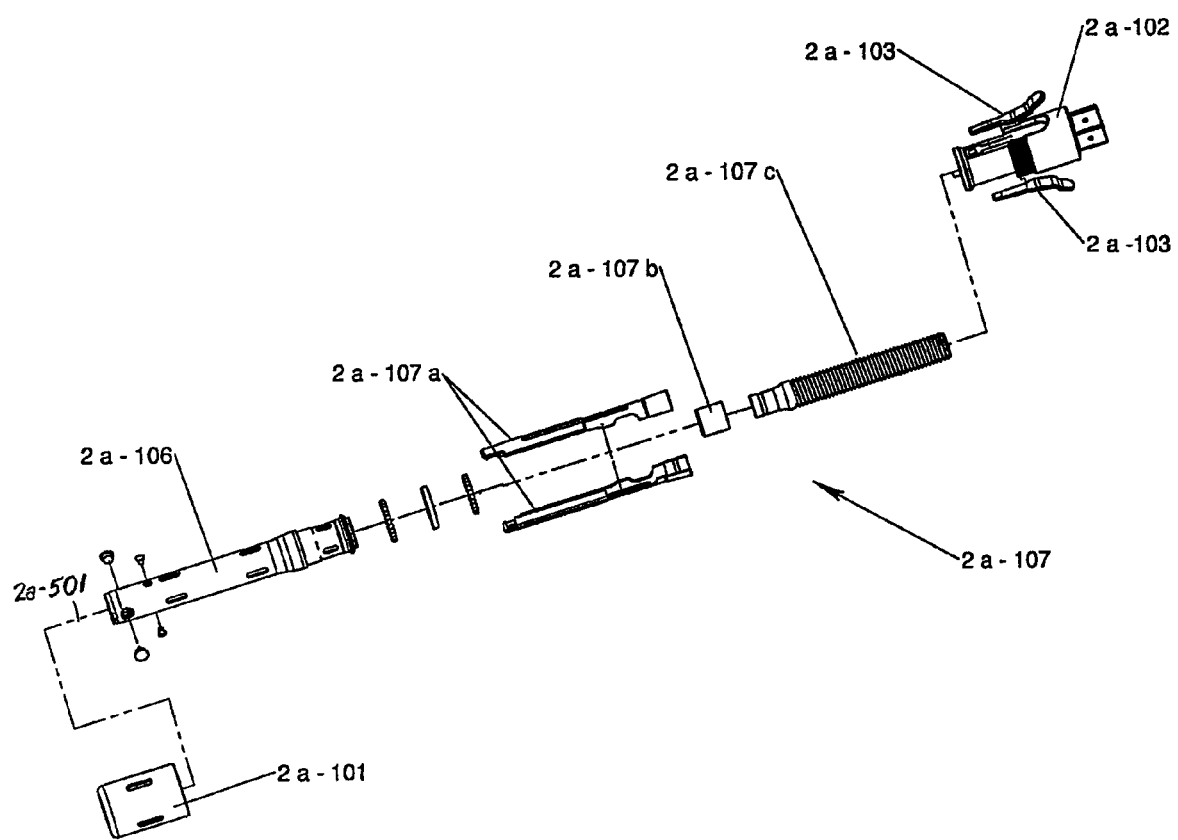

Referring to FIG. 2, the complete reducer/inserter apparatus is shown in an exploded view with the main components disassembled. The exploded view shows the main assemblies and members that will typically be presented to the surgeon in the operating room. In the preferred embodiment, the reducer assembly 2-1 is the first component to be utilized by the surgeon to reduce the spinal rod onto the tulip assembly.

Figure 28:
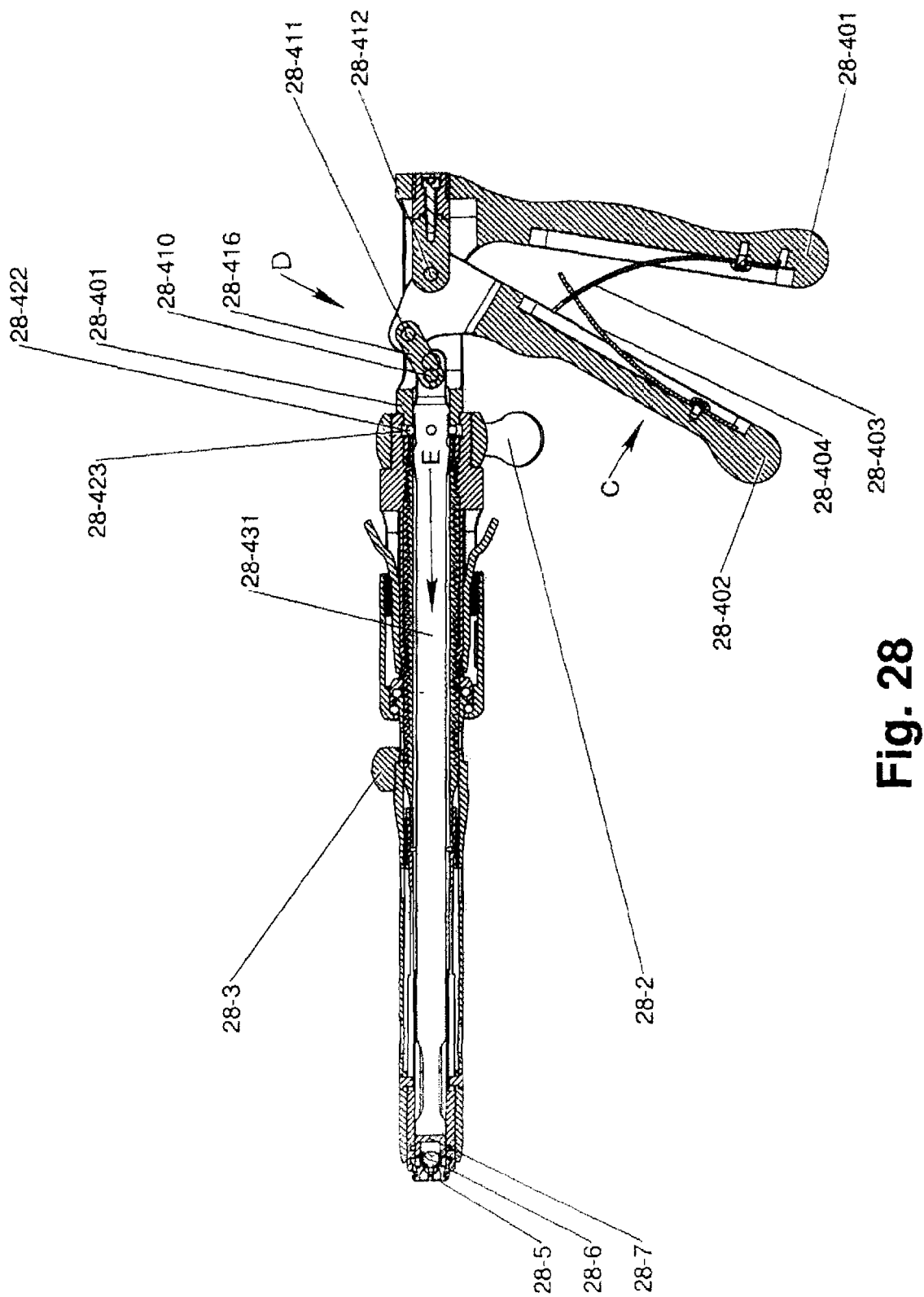
FIG. 28 is a front sectional view of the complete reducer and cap inserter assembly in the cap seated to initial position.

The torque handle 2-2 will be placed on the reducer assembly 2-1 as shown by the dashed lines when the resistance force against the reduction of the rod increases and additional torque is required. The torque handle 2-2 slides onto the proximal torque handle attachment structure or drive nut portion 2-104 of the reducer assembly, and includes a passage 2-12 configured to non-rotatably mate with the drive nut 2-104 so that when assembled rotation of the torque handle causes rotation of the drive nut, activating a drive mechanism (explained in detail below). As shown, the passage 2-12 and attachment structure 2-104 are hexagonal, although other configurations are possible. During the last stages of the reduction process (discussed in greater detail subsequently) the reducer assembly 2-1 will tend to rotate out of position due to the large amount of torque that must be applied to the torque handle 2-2. The counter torque handle 2-3 component then will be added to the apparatus to stabilize the device and minimize rotation of the reducer assembly 2-1 out of position. The anti-torque handle of the reducer assembly 2-1 is applied to the shaft assembly of the reducer assembly at an anti-torque handle attachment structure 2-105 that is rotatable with respect to the torque handle attachment structure 2-104. The anti-torque handle attachment structure or collar 2-105 and an attachment portion or jaw 2-31 of the anti-torque handle fit together so that the jaw and collar do not rotate relative to one another. Applying force to the anti-torque handle 2-3 in a rotary direction opposite the rotation of the torque handle 2-2 stabilizes the reducer assembly 2-1 and minimizes rotation or deformation of the clamp portion 2-20 during rotation of the torque handle 2-2. Finally, the cap inserter assembly 2-4 will be inserted into the throughbore 2-15 along the central axis of the reducer assembly 2-1 as indicated by the dashed line in FIG. 2 to drive the locking cap axially toward a clamp portion 2-20 at the distal end of the reducer assembly in order to lock a cap member held by the insert assembly 2-4 to a tulip assembly held by the clamp portion 2-20 (as shown in FIG. 28). In order to prevent the cap inserter assembly from backing out of the reducer assembly as it drives the cap toward the tulip, the inserter assembly may be provided with a locking mechanism to secure its position with respect to the reducer assembly, as will be explained further below.

The main components, as shown in FIG. 2, can be assembled in any order based on the user's preference. Manifestly, alternative geometries for the torque and counter torque handles (2-2 and 2-3 respectively) are possible. For example, the handles could have a "T" or "L" shape to provide the operator with the desired leverage.

Figure 3:
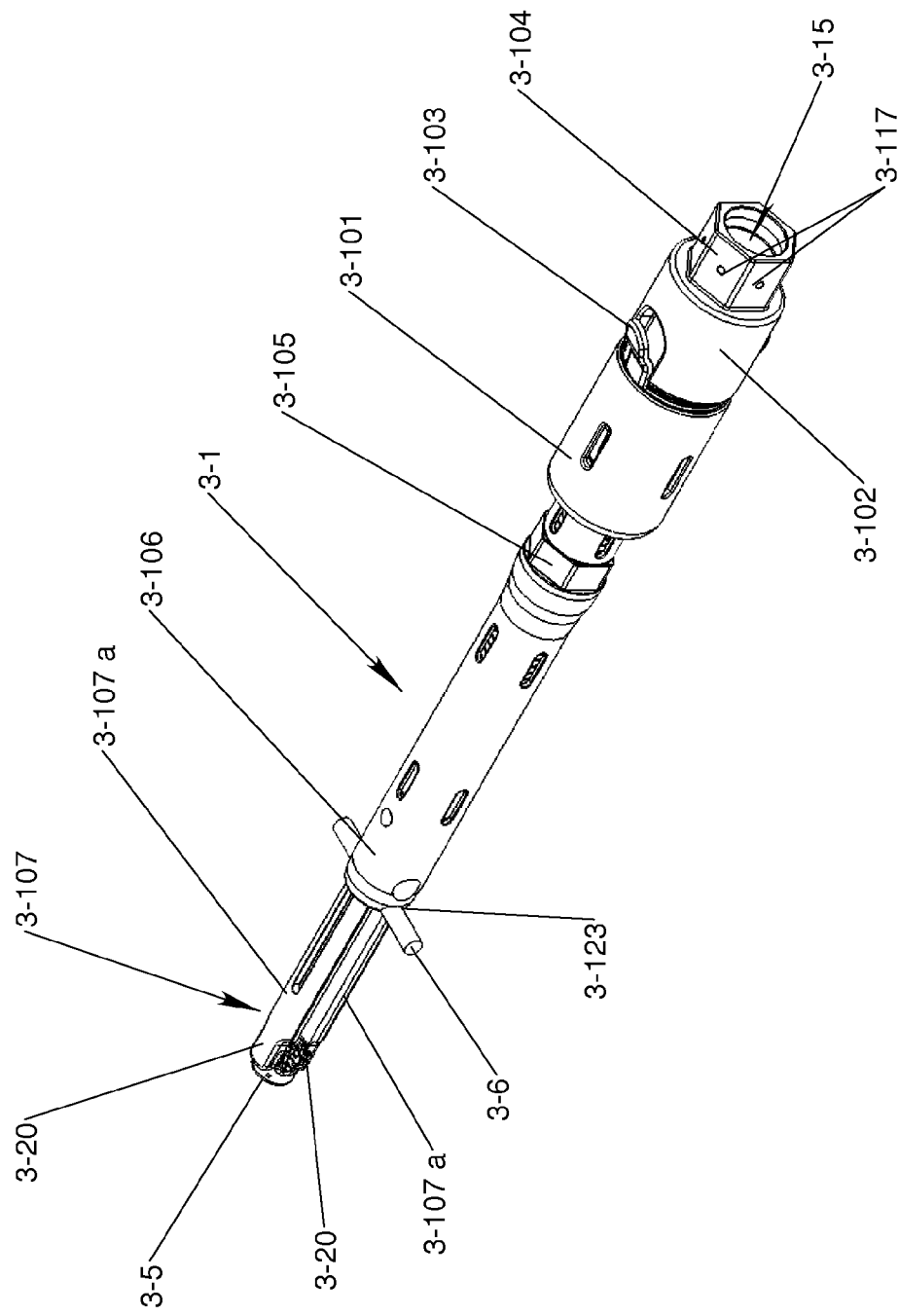
FIG. 3 is a perspective view of the reducer tool assembly in the initial position prior to insertion of the cap insert assembly.

Referring to FIG. 3, the reducer assembly 3-1 is shown with a tulip assembly 3-5 secured thereto by the distal clamp portion 3-20 thereby. The outer shaft assembly 3-106 alternatively may provide a different bearing shape for the spinal rod 3-6 or holding mechanism for the spinal rod 3-6. For example, a bumper material or support beam could be placed between the spinal rod 3-6 and the outer shaft member 3-106 to prevent accidental notching of the spinal rod 3-6. For example of different holding mechanisms, a spring clip or friction fit arrangement could be attached to the outer shaft assembly 3-106 to secure the spinal rod 3-6 during the reduction procedure.

The reducer assembly 3-1 includes an inner shaft assembly 3-107, an outer shaft member 3-106, and a drive housing 3-102. The inner shaft assembly 3-107 (shown in greater detail in FIG. 11) includes elongate tulip attachment members 3-107a between which the tulip member 3-5 can be secured. The outer shaft member 3-106 has a cylindrical sleeve configuration sized to fit about the inner shaft assembly 3-107. The inner shaft assembly 3-107 and outer shaft member 3-106 shift axially with respect to each other in order to shift a spinal rod 3-6 along the axis of the reducer assembly 2-1 and toward the tulip assembly 3-5 secured thereto.

The elongate tulip engaging arms 3-107a are bent slightly radially outward near their proximal ends so that they are slightly splayed. The splayed arms are shifted toward one another as the sleeve-like outer shaft member 3-106 begins to shift over the arms 3-107a, applying a radially compressive force thereto.

When the inner shaft assembly 3-107 is fully shifted in the distal direction the two tulip engaging arms 3-107a of the inner shaft assembly 3-107 splay or open so that the spacing therebetween is sized to accept the tulip assembly 3-5 therein. In order to reduce or shift a spinal rod into a tulip assembly, the reducer assembly 3-1 is oriented so that the elongate tulip engaging arms 3-107a are disposed on opposite sides of a spinal rod 3-6 and the splayed clamp portions 3-20 of the inner shaft assembly 3-107 are disposed about the tulip assembly 3-5.

A slight shifting of the inner shaft assembly 3-107 in the proximal direction, so that the outer shaft member 3-106 begins to shift over the proximal ends of the tulip engaging arms 3-107a, causes the clamp portions 3-20 of the arms 3-107a to clamp the tulip assembly 3-5 therebetween. Further shifting of the outer shaft member 3-106 in the distal direction causes the outer shaft member 3-106 to abut the spinal rod 3-6 disposed between the arms 107a, and drives a spinal rod 3-6 between the arms 107a into the tulip assembly 3-5. The illustrated outer shaft member 3-106 includes arcuate recesses 3-123 to engage and guide the rod 3-6.

Figure 4:
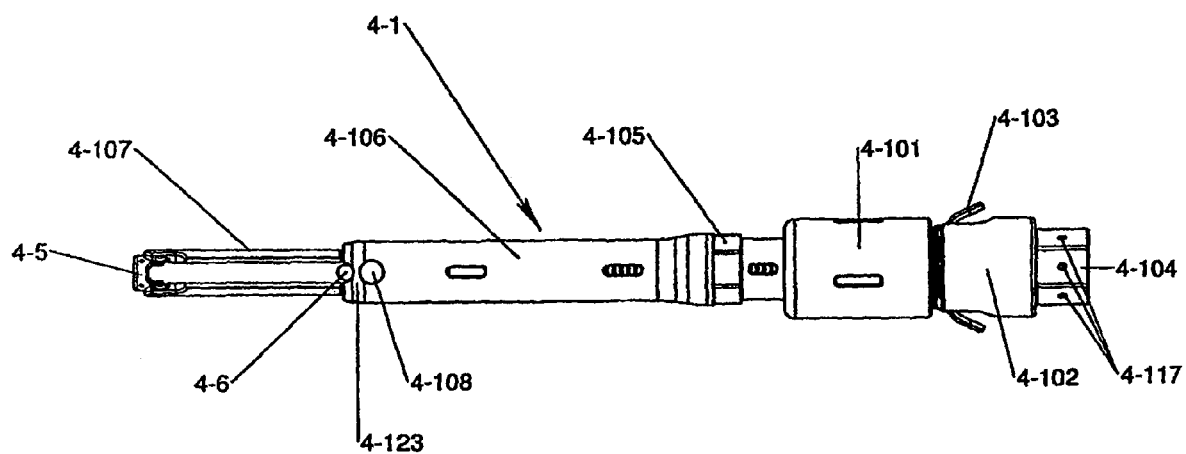
FIG. 4 is a front elevational view of the reducer assembly of FIG. 3.
Figure 5:
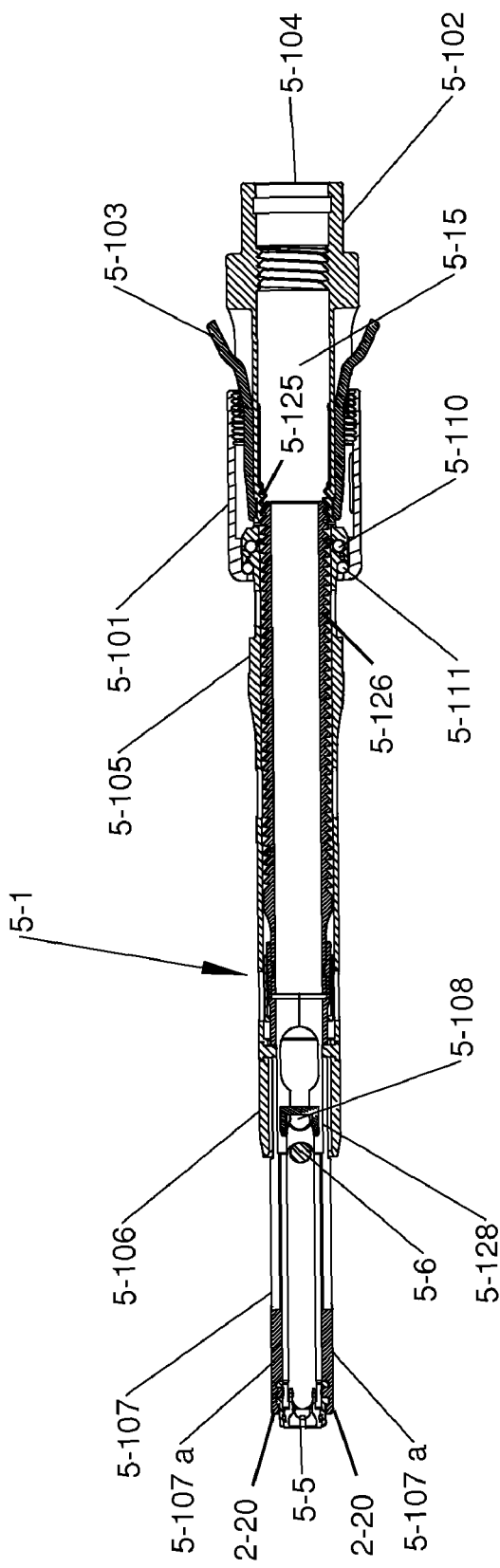
FIG. 5 is a front sectional view of the reducer assembly in the initial position.

Alternatively, the inner shaft assembly 3-107 may be initially arranged in a clamping configuration and subsequently be shifted to an open configuration so that the arm clamp end portion 3-20 splay apart as the outer shaft member 3-106 moves in the proximal direction with respect to the inner shaft member. For instance, a splay member may be operatively connected to the outer shaft member and disposed between the arms of the inner shaft assembly and configured to wedge between the arms, splaying the arms apart as it travels backwardly therebetween so that the arms can receive the tulip assembly. For instance, in one form, as shown in FIG. 4, an expansion pin 4-108 is shown carried by the outer shaft member 4-106 and extending transversely thereto. As best shown in FIG. 5, expansion pin 5-108 causes the inner shaft assembly 5-107 walls to splay or shift radially outward when the expansion pin 5-108 is shifted to a narrow slot portion 5-128 where the gap between the tulip engaging arms 5-107a is narrow, allowing receipt of the tulip 5-5 in the inner shaft assembly 5-107. As the inner shaft assembly 5-107 shifts in the proximal direction relative to the outer shaft member 5-106, the expansion pin 5-108 moves away from the narrow portion 5-128, allowing the walls of the inner shaft assembly 5-107 to resiliently shift back radially inward to clamp about and hold the tulip 5-5. The expansion pin 4-108 may be connected to the outer shaft member 4-106, for instance by laser welding. The arms 4-107 may also be shifted by a combination of the expansion pin 4-108 applying an outward splay force when the inner shaft assembly 4-107 and outer shaft member 4-106 are in a first position, and the outer shaft member 4-106 applying a radial inward clamping force on the arms 4-107a when the inner shaft assembly 4-107 and outer shaft member 4-106 are in a second position. Other configurations to cause radial shifting of the clamp portions 3-20 of the inner shaft member for receiving a tulip assembly are also possible.

A drive system is provided in order to shift the inner shaft assembly and outer shaft member relative to each other. In the illustrated embodiment, the reducer assembly drive system is located toward the proximal end of the apparatus. The drive system includes a drive cover 3-101, a drive housing structure 3-102, and a drive release mechanism 3-103, which are all mechanically coupled and able to rotate about the instrument axis. Rotation of the drive housing 3-102 causes the inner shaft assembly 3-107 to shift axially with respect to the outer shaft member 3-106.

The torque handle 2-2 assists in rotation of the drive system. The drive nut 3-104 for the torque handle can be seen at the proximal end of the apparatus in FIG. 3. The nut structure 3-104 in the illustrated form has a hexagonal configuration including six flat surfaces each with a recess or dimple 3-107 formed therein. These recesses or dimples assist in the attachment of the torque handle 2-2, as described in greater detail with respect to FIG. 8.

The drive system may include a motor assembly, although manual manual operation of the apparatus will primarily be described herein. Examples of motor assemblies that could be used are an electric motor, hydraulic motor, or pneumatic motor.

Referring to FIG. 4, the reducer assembly is shown clamped to the tulip assembly. In the preferred embodiment, the outer shaft member 4-106 has a concave notch or groove in the form of arcuate recess 4-123 configured to receive and seat the spinal rod 4-6 therein. Also, the recesses or dimples located on the faces of the drive nut structure 4-104 can also be seen in the front view of FIG. 4.

With continued reference to FIG. 5, the reducer assembly 5-1 is shown in the clamped position with the tulip assembly 5-5 tightly held between the end clamp portions 2-20 of the inner shaft arm, 5-107a. In the preferred embodiment, the inner shaft assembly 5-107 is mechanically constrained by the outer shaft member 5-106 and operatively connected to the drive release mechanism 5-103 with threads 5-125 and 5-126, such as buttress threading. The release mechanism 5-103 of the drive housing 5-102 is connected to the inner shaft assembly 5-107 so that rotation of the drive housing 5-102 shifts the housing 5-102 linearly along the inner shaft 5-107. Since the reducing sleeve or outer shaft member 5-106 is rotatably coupled to the drive housing 5-102, rotation of the drive housing also shifts the outer shaft member 5-106 linearly without rotation with respect to the inner shaft member 5-107 to reduce the spinal rod 5-6 toward the tulip member 5-5.

Figure 6:
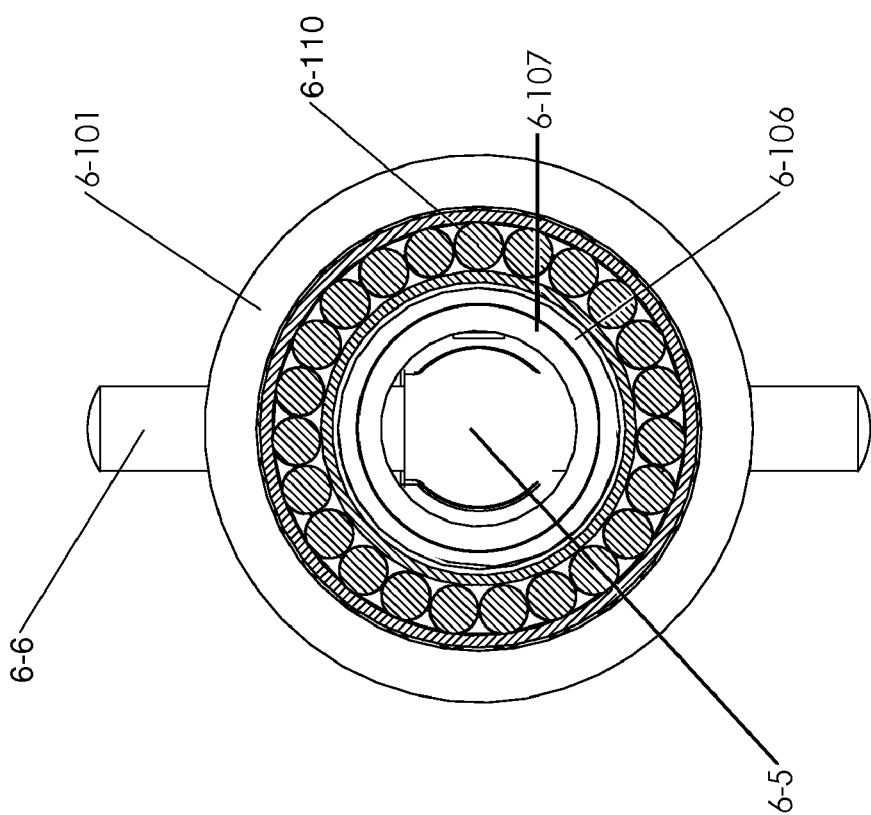
FIG. 6 is a side partial sectional view of the reducer assembly in the initial position.
Figure 7:
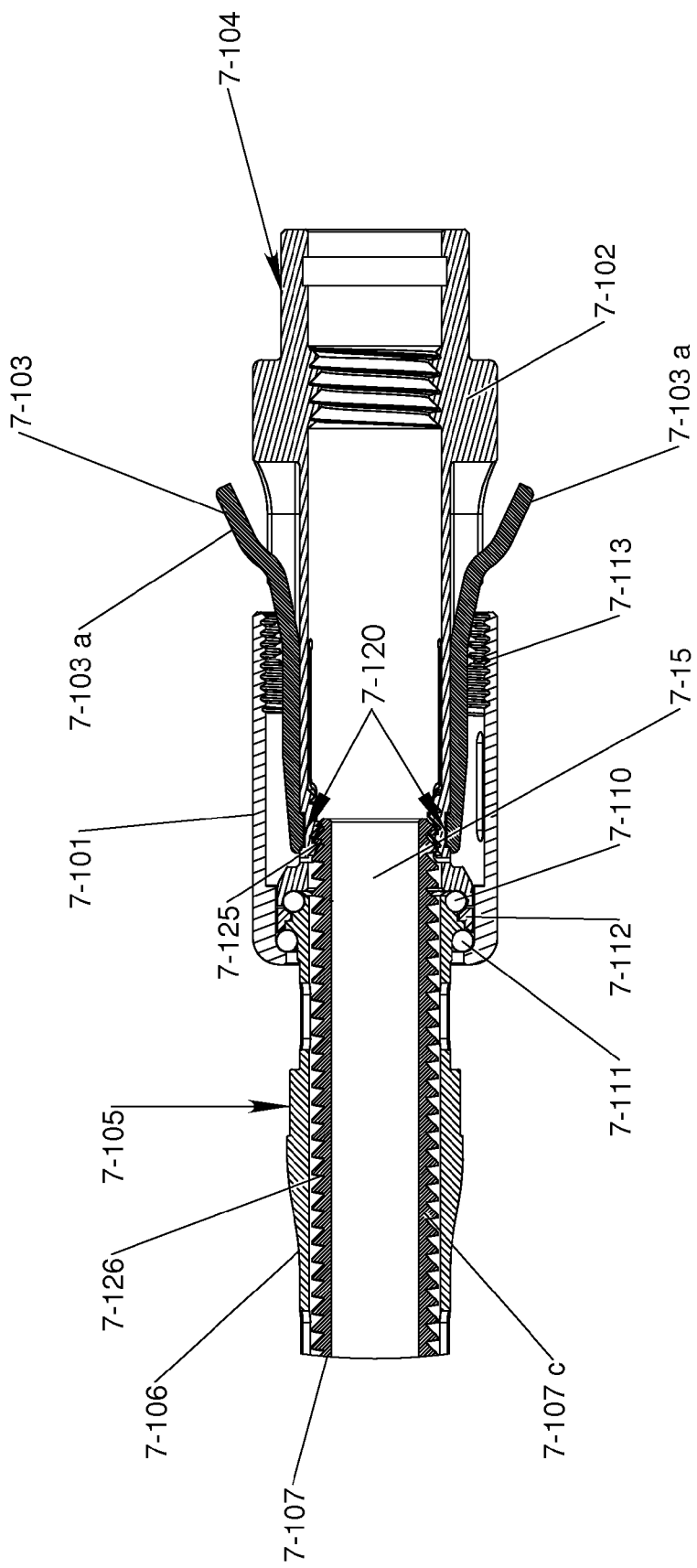
FIG. 7 is a detailed front sectional view of the reducer assembly in the initial position.

Optionally, bearing members 5-110 and 5-111 may be provided to minimize galling or wear on the outer shaft member 5-106 and the drive cover 5-101 as they are rotated with respect to one another. More detailed views of the bearing members is shown in FIGS. 6 and 7. In the illustrated form, a plurality of bearing members in the form of ball bearings are arranged around the circumference of the outer shaft member 6-106. When the reduction of the spinal rod 5-6 meets high resistance from the patient's body (as the rod and tulip assembly are drawn together, as in FIGS. 12 through 18), the ball bearings reduce friction on the threads to avoid binding of the reducer/inverter device and allow manual operation of the device to continue during a surgical procedure. The bearing members 5-110 and 5-111 are preferably ceramic spheres to provide corrosion resistance during the sterilization process of the reducer/inserter apparatus.

Referring to FIG. 6, the concentric arrangement of the bearing members 6-110 is illustrated. In the preferred embodiment, the circular profile of the reducer/inserter apparatus can be clearly seen in FIG. 6. The radially outer orientation of the drive cover 6-101 is shown in relation to the outer and inner shaft assemblies 6-106 and 6-107 respectively. The drive cover 6-101 can rotate relative to the outer and inner shaft assemblies (6-106 and 6-107) and friction therebetween is reduced by the ball bearing members 6-110. Although not shown in FIG. 6, another set of ball bearings may be included, such as bearings 5-111 in FIG. 5. The bearing members 5-110 and 5-111 are separated by a bearing retainer shown in FIG. 7.

The drive cover 7-101 is fixed to the drive housing structure 7-102 by a thread seam 7-113. Epoxy may be applied within the thread seam 7-113 to create a single or unitary continuous drive element.

Alternatively other types of bearing systems may be used. Examples of alternative bearing systems include roller bearings or sleeve bearings.

Referring to FIG. 7, the drive system of the reducer assembly is shown in the initial position so that the tulip engaging arms are shifted to their fully extended position relative to the outer shaft member. In a preferred embodiment, the inner shaft assembly 7-107 has buttress threads 7-125 and 7-126 that form a 90 and 45 degree angle as shown in FIG. 7. The buttress threads allow for high loads to be applied thereto yet allow quick advancement of the inner shaft assembly if necessary.

The drive housing 7-102 is rotated to shift the housing linearly up and down the inner shaft member 7-107 by interaction between interior threads 7-120 on the drive housing and exterior threads 7-125 on the inner shaft member. Since the drive cover 7-101 is fixed to the drive housing 7-102, rotation of the drive housing rotates and linearly shifts the drive cover. A shoulder of the outer shaft member 7-105 extends radially outward and in-between the drive cover 7-101 and drive housing 7-102 (and between two sets of circumferentially arranged bearings 7-110 and 7-111), rotatably coupling the outer shaft member to the drive system. Bearings 7-110 and 7-111 assist in smooth rotation of the drive housing 7-102 and cover 7-101 with respect to the outer shaft member 7-105. Due to this rotatable coupling, the outer shaft member 7-105 is shifted linearly without rotation over the inner shaft member 7-107 during rotation of the drive housing 7-102. When the drive housing is rotated in a first direction, the drive housing and bearings 7-110 will push down on the shoulder of the outer shaft member 7-105. When the drive housing is rotated in a reverse direction, travelling upward along threads 7-125, the associated drive cover 7-101 and bearings 7-111 will push upward on the shoulder of the outer shaft member 7-105, shifting the outer shaft member upward. In this manner, the drive housing is manipulated to cause the outer shaft member 7-105 to capture and reduce a spinal rod.

As previously described, the interior threads at the distal ends of the tab projections 7-103a of the drive release mechanism in 7-103 can be disengaged if the proximal ends of tab projections 7-103a are depressed axially inward by the operator, causing the tab distal ends, including the threads therein, to shift radially outward and disengage from the external threads 7-107c on the inner shaft member, allowing the inner shaft member 7-107 to be linearly advanced quickly and without rotation. In other words, the depression of the tabs allows for non-threaded shifting of the inner and outer shafts relative to each other to allow quick positioning of the inner shaft assembly 7-107.

The tabbed drive release mechanism 7-103 may be integrally connected to the drive housing structure 7-102, for instance by a laser weldment. The drive release mechanism 7-103 operates to release the threads 7-125 of the housing structure 7-102 from the threaded reduction driver member 7-107c of the inner shaft assembly 7-107, when the operator of the device, typically the surgeon, applies a radially inward pushing force on the two tabs 7-103a of the drive release mechanism 7-103 that extend from the drive housing structure 7-102. The release of the threads then allows the surgeon to shift the spinal rod via rapid axial shifting of the inner shaft drive member and toward the tulip assembly when minimal drive force is required for this purpose.

The use of the drive release mechanism 7-103 therefore provides a more ergonomic design that reduces the strain and repetitive motion injury to the surgeon by reducing the number of times the surgeon is required to apply repetitive rotational force to reduce the spinal rod onto the tulip member 5-5. The ergonomic design also increases the speed of operation of the spinal reduction surgery, and reduces time of the patient under anesthetic. The reduction of the time the patient is under anesthetic correspondingly reduces the risk of infection, the risk of complications from the anesthetic itself, and the recovery time of the patient.

Alternatively, other drive systems may be used to advance the outer shaft member 7-106 with respect to the inner shaft assembly 7-107. In addition, other types of screw threads may be used, such as those used for power threads. Examples of power threads include acme, UNC, or UNF threads. However, almost any kind of threading system may be used, including a ball screw. Other types of drive systems that could be used to drive the inner shaft assembly 7-107 include ratchet systems or friction drives.

Figure 8:
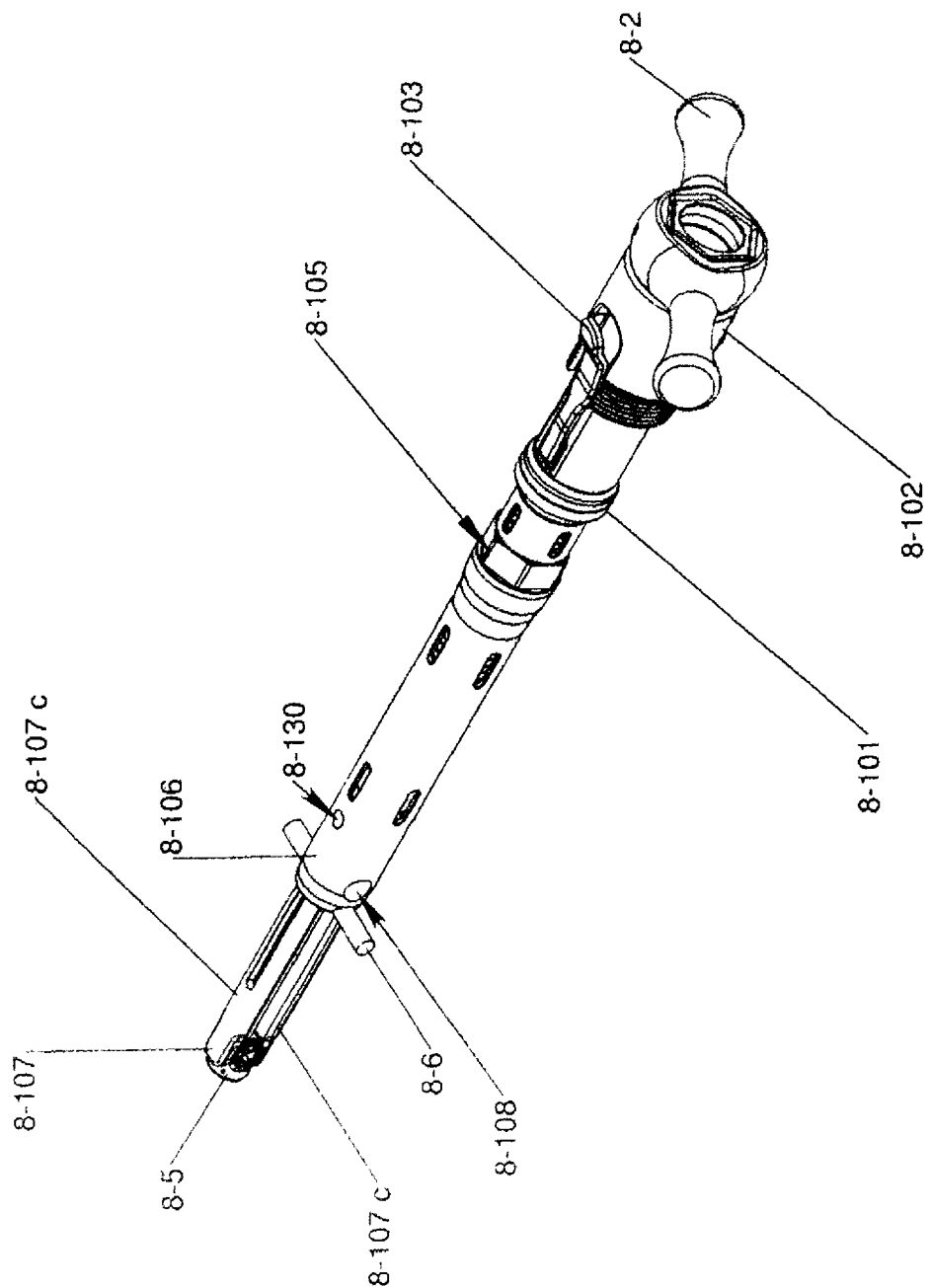
FIG. 8 is a perspective view of the reducer assembly and torque handle in the rod engaged position.

Referring to FIG. 8, the reducer assembly is shown in an isometric view with the torque handle added. The illustrated torque handle 8-2 shifts into position over the hexagonal shape of the attachment nut structure 8-104 of the drive mechanism. The torque handle has a female hexagonal passage in which the attachment structure 8-104 may be disposed. A detent configuration may be provided to aid in securing the torque handle 8-2 to the attachment structure 8-104. For instance, the torque handle 8-2 may have a set screw with a spring loaded bearing pin (not shown) that springs into position to mate with dimples or recesses 4-117 on the hexagonal faces of the attachment structure 4-104. The pin assists in providing a secure connection between the torque handle 8-2 and the attachment structure 8-104 with which it mates.

In the preferred embodiment, the operator of the reducer/inserter apparatus applies rotational force to the torque handle 8-2 which drives the linear motion of the outer shaft member 8-106 along the inner shaft assembly and creates a linear force for driving the spinal rod 8-6 into position over the tulip member 8-5.

In FIG. 8, an anti-rotation member in the form of an alignment pin 8-130 is shown. Alignment pins 8-130 are located in each side of the assembly, exiting from the outer shaft member 8-106 and into elongate axial slots or windows in each arm 8-107c of the inner shaft member to keep the inner shaft assembly 8-107 from rotating. However, the alignment pins 8-130 allow the inner shaft assembly 8-107 to shift or slide axially, allowing for travel of the inner shaft assembly 8-107 in the proximal and distal directions. Each alignment pin 8-130 is short enough so as not to obstruct the central passage of the reducer assembly, and may be laser welded or otherwise fixed to the outer shaft member 8-106.

In alternative embodiments, the function of the alignment pin 8-130 could be achieved mechanically with other systems. Examples of alternative systems include a tongue and groove arrangement or types of threading between the inner shaft assembly 8-107 and the outer shaft assembly 8-106 to prevent rotation between the aforementioned parts.

Figure 9:
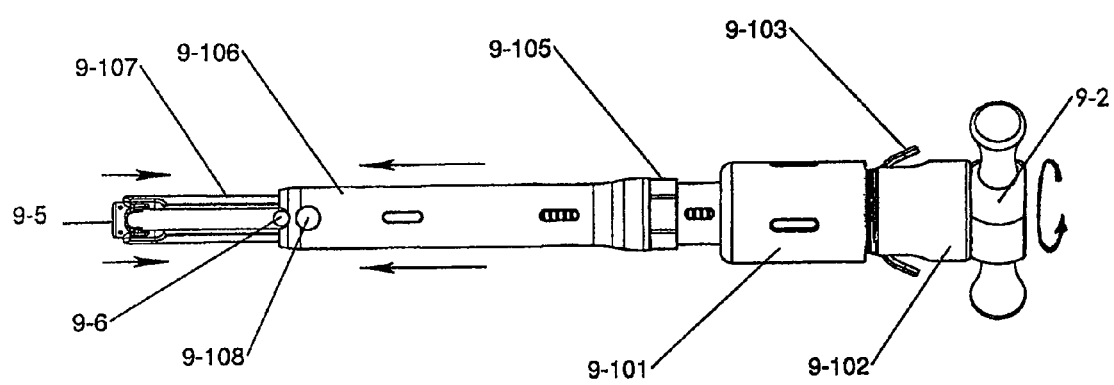
FIG. 9 is a front elevational view of the reducer assembly and torque handle in the rod engaged position.

As shown in FIG. 9, the torque handle is rotated so that the inner shaft assembly 9-107 and outer shaft member 9-106 have shifted with respect to each other, reducing the distance between the spinal rod 9-6 engaged by the outer shaft member 9-106 and the tulip assembly 9-5 secured to the inner shaft assembly 9-107. Typically, once the outer shaft member 9-106 has shifted to the position shown in FIG. 9, the spinal rod 9-6 will be kept in place by the resistance force provided by the patient's body. From this point in the surgical procedure onward the resistance force required to reduce the spinal rod 9-6 to the tulip member 9-5 will increase significantly.

Figure 10:
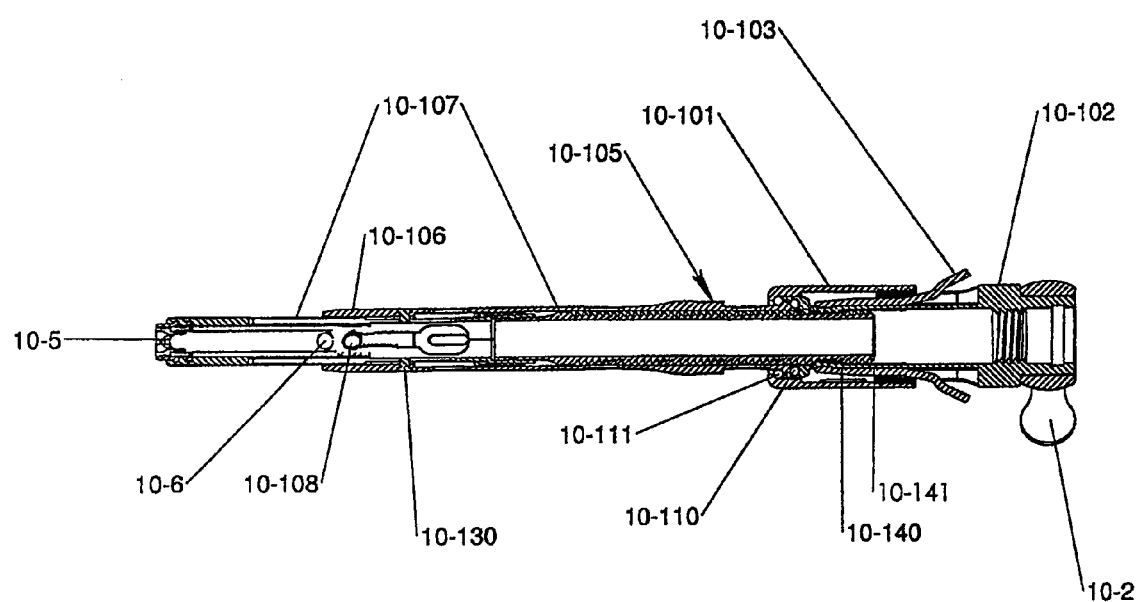
FIG. 10 is a front sectional view of the reducer assembly and torque handle in the rod engaged position.

FIG. 10 demonstrates the shifting of the assembly to the position shown in FIG. 9. A benchmark reference point 10-140 is shown representing the position that the proximal end of the inner shaft assembly 10-107 reaches when the inner shaft assembly 10-107 is fully extended in the distal direction for receipt of the tulip assembly. When the apparatus is in the position shown in FIGS. 9 and 10, the proximal end of the inner shaft assembly 10-107 is retracted internally to the reference point 10-141. As can be seen by FIG. 10, the inner shaft assembly 10-107 has retracted only slightly into the outer shaft member 10-106, drawing the tulip assembly 10-5 slightly toward the spinal rod 10-6.

In alternative embodiments, the arrangement of the shafts can be altered yet accomplish the same function. For example, the functions of the outer shaft member and inner shaft assembly can be exchanged. In other words, the mere changing of the functioning of the different shifting shafts is contemplated in this invention.

Figure 11:
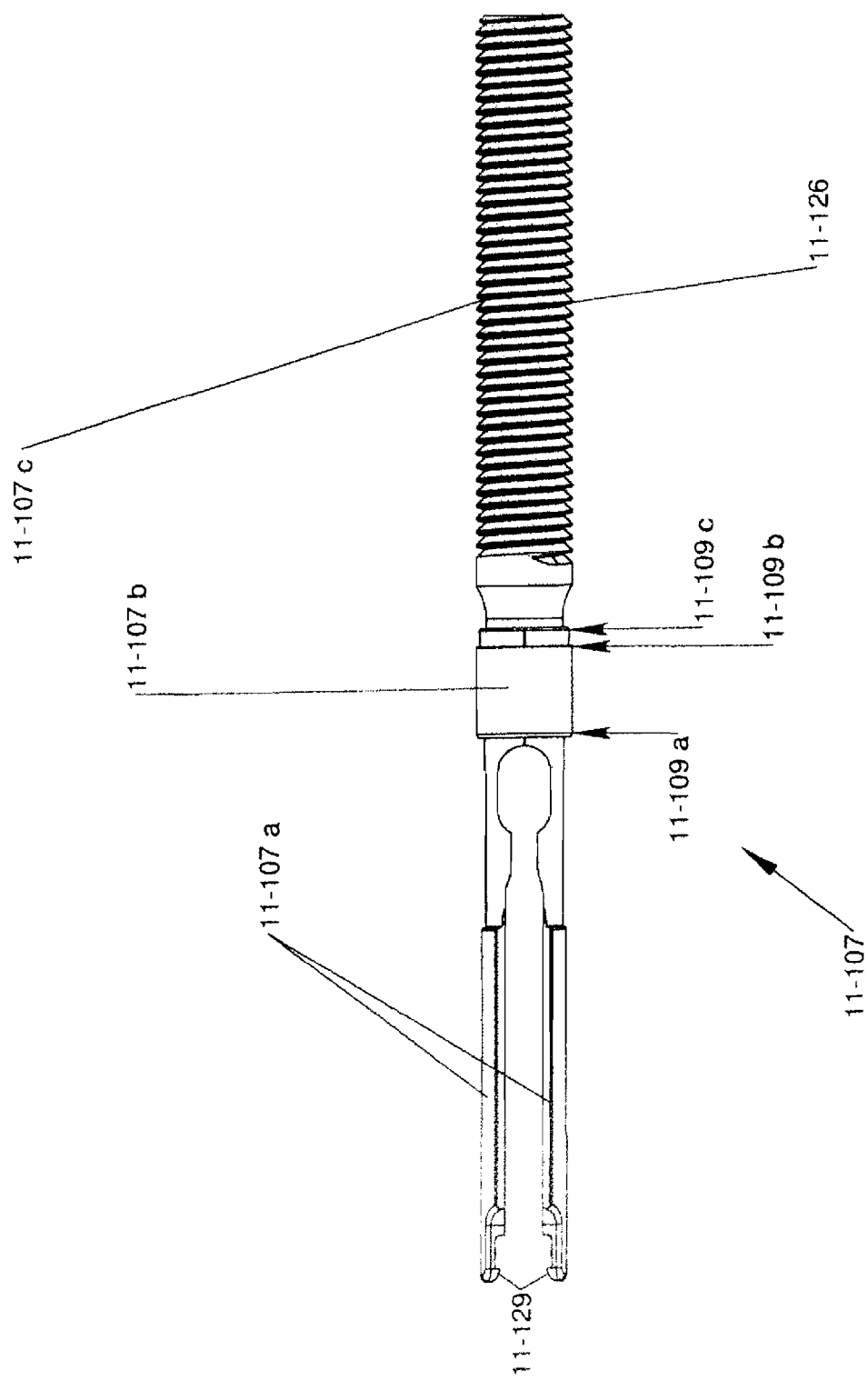
FIG. 11 is a front elevational view of the inner shaft assembly.

The inner shaft assembly is shown in detail in FIG. 11. In the illustrated embodiment, the inner shaft assembly 11-107a is structurally formed by connecting two tulip attachment members 11-107, and the reduction driver member 11-107c using the axially intermediate inner shaft support member 11-107b. The inner shaft assembly 10-107 may be formed as a unitary body, or may comprise multiple components that may be laser welded at weldments 11-109 a, b, and c or otherwise fixed together to create a single unitary assembled component.

In one embodiment, the tulip attachment member 11-107a is connected to the inner shaft support member 11-107b by laser weldment 11-109a. The inner shaft support member or collar 11-107b then provides structural support and a connection to the reduction driver member 11-107c. The inner shaft support member 11-107b is held to the reduction driver member 11-107c, for instance by a laser weldment 11-109b. The reduction driver member 11-107c also may be directly welded to the proximal portion of the tulip attachment arm members 11-107a projecting axially through and beyond the attachment collar 11-107b with a weldment 11-109c.

The reduction driver member 11-107 includes threads 11-126 which interact with threads on the drive mechanism as rotational force is applied by the operator to the torque handle 8-2, shifting the drive mechanism reduction driver member 11-107c and the rest of the inner shaft assembly 11-107.

A flange 11-129 at the distal end of each tulip engaging arm 11-107a is provided to engage the tulip assembly 10-5. The flanges are arranged to extend radially inwardly so that they are configured to maintain the tulip assembly 10-5 in position between the arms 11-107a under high loads, and may be formed integral to the tulip engaging arms for added strength.

In alternative embodiments, the fabrication of the inner shaft assembly 11-107 could be accomplished by fabricating a single part by other manufacturing techniques. For example, stamping, wire Electric Discharge Machining (EDM), investment casting, forging, or cold rolling could all be used to provide the precise machining required of the fine flange on the tulip attachment member 11-107a.

Figure 12:
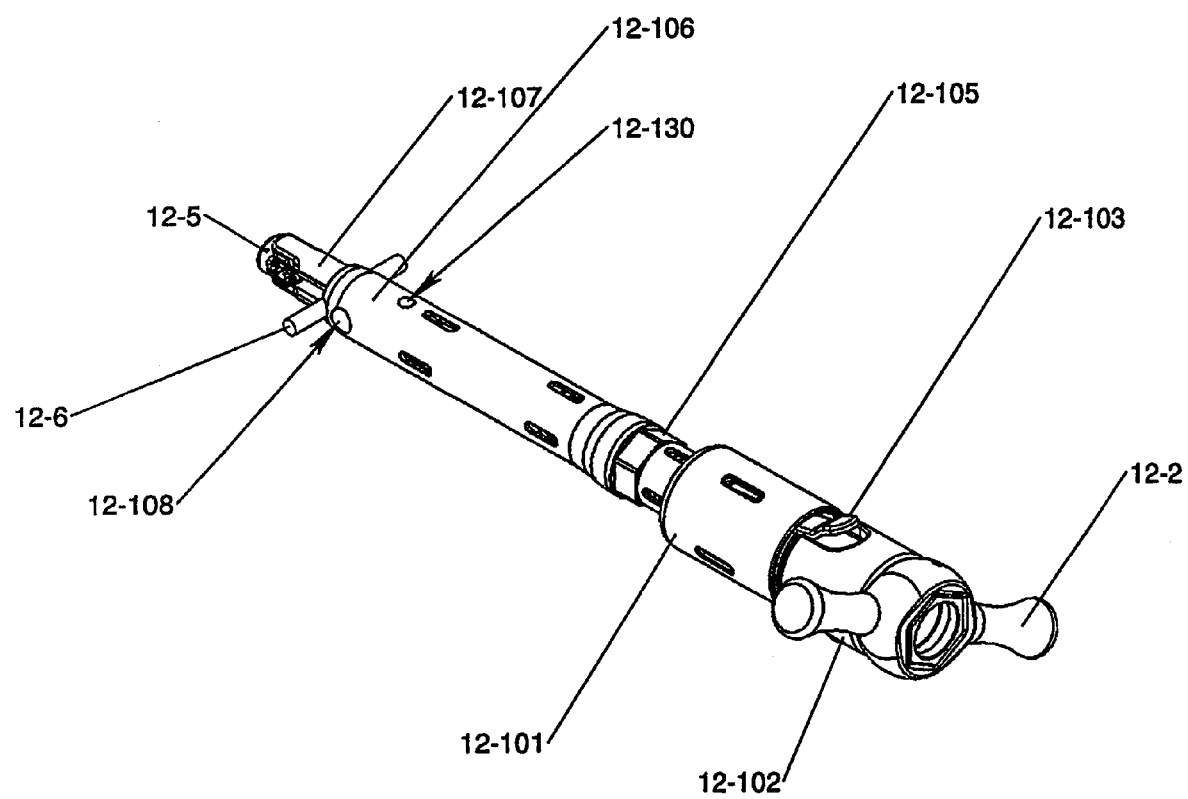
FIG. 12 is a perspective view of the reducer assembly and torque handle in the intermediate position.
Figure 13:
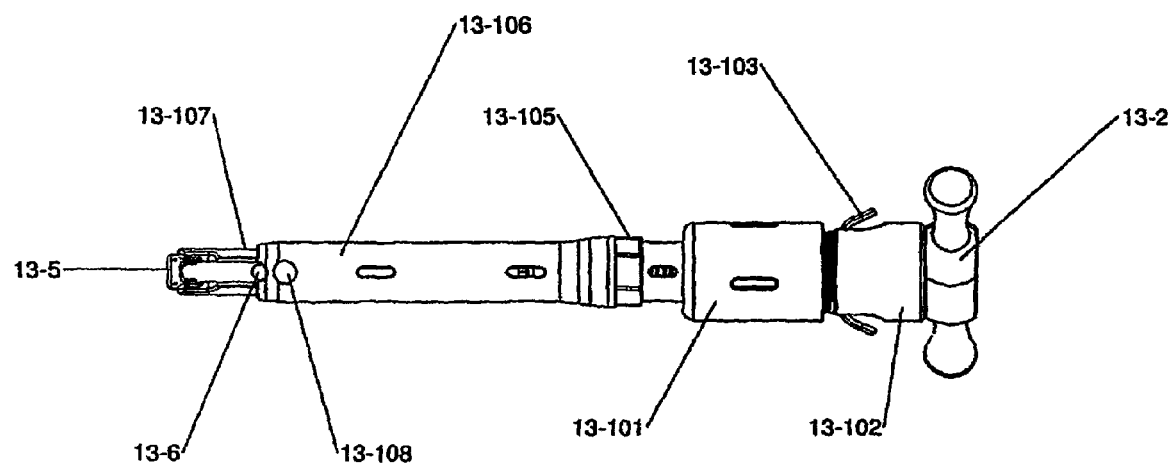
FIG. 13 is a front elevational view of the reducer assembly and torque handle in the intermediate position.

Referring to FIG. 12, the reducer assembly including the torque handle are shown with the rod further reduced. The inner shaft assembly 12-107 has been retracted significantly into the outer shaft member 12-106 as the reduction procedure has significantly progressed, as shown by comparison of FIG. 8 and FIG. 12. This further reduction is also shown in a front view in FIG. 13. A comparison of FIG. 9 and FIG. 13 demonstrates the shifting of the rod 9-6 toward the tulip assembly 9-5. This position is also shown in the cross-sectional view of FIG. 14. The benchmark reference point 14-140 is the position the proximal end of the inner shaft assembly 14-107 reaches when the inner shaft assembly 10-107 is fully extended in the distal direction. When the apparatus is in the intermediate position of FIG. 14, the proximal end of the inner shaft assembly 14-107 is further retracted internally past reference point 141 (the position of the inner shaft in FIG. 10) to reference position 14-142. Typically, at this point in the reduction process the spinal rod 14-6 is being forcefully driven into the tulip member 14-5 and significant force is needed to reduce the spinal rod 14-6 further.

Figure 14:
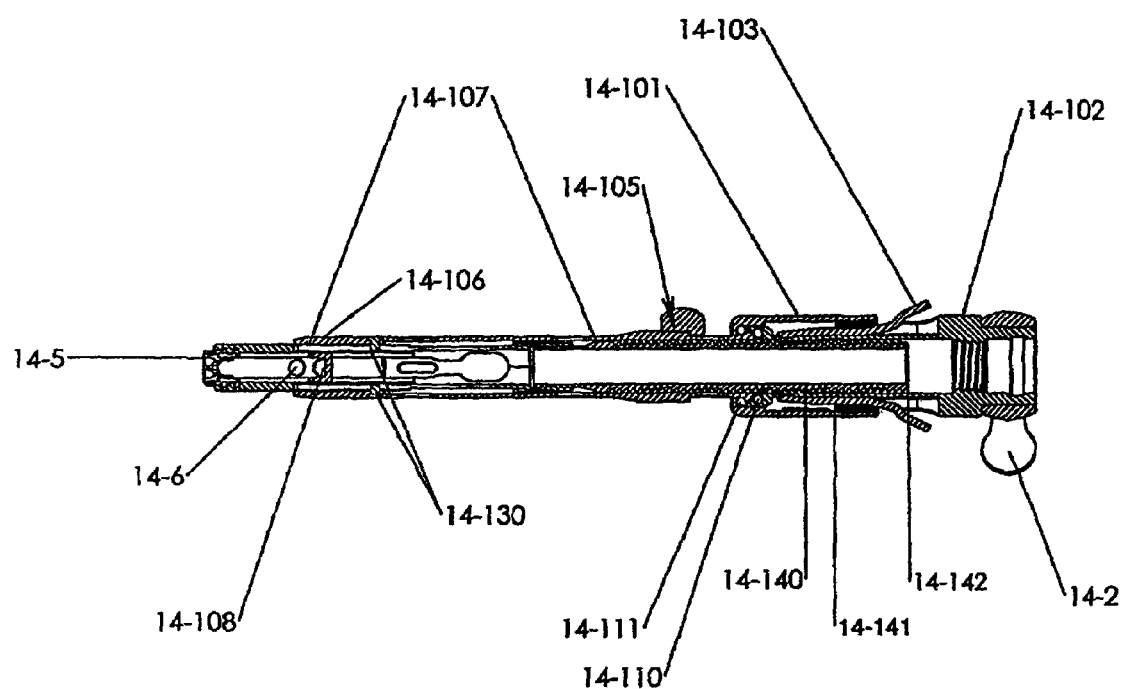
FIG. 14 is a front sectional view of the reducer assembly and torque handle in the intermediate position.

The positioning of the alignment pin 14-130 is shown in FIG. 14. Again, the alignment pin 8-130 maintains the alignment of the inner shaft assembly 8-107 or keep the inner shaft assembly 8-107 from rotating.

Figure 15:
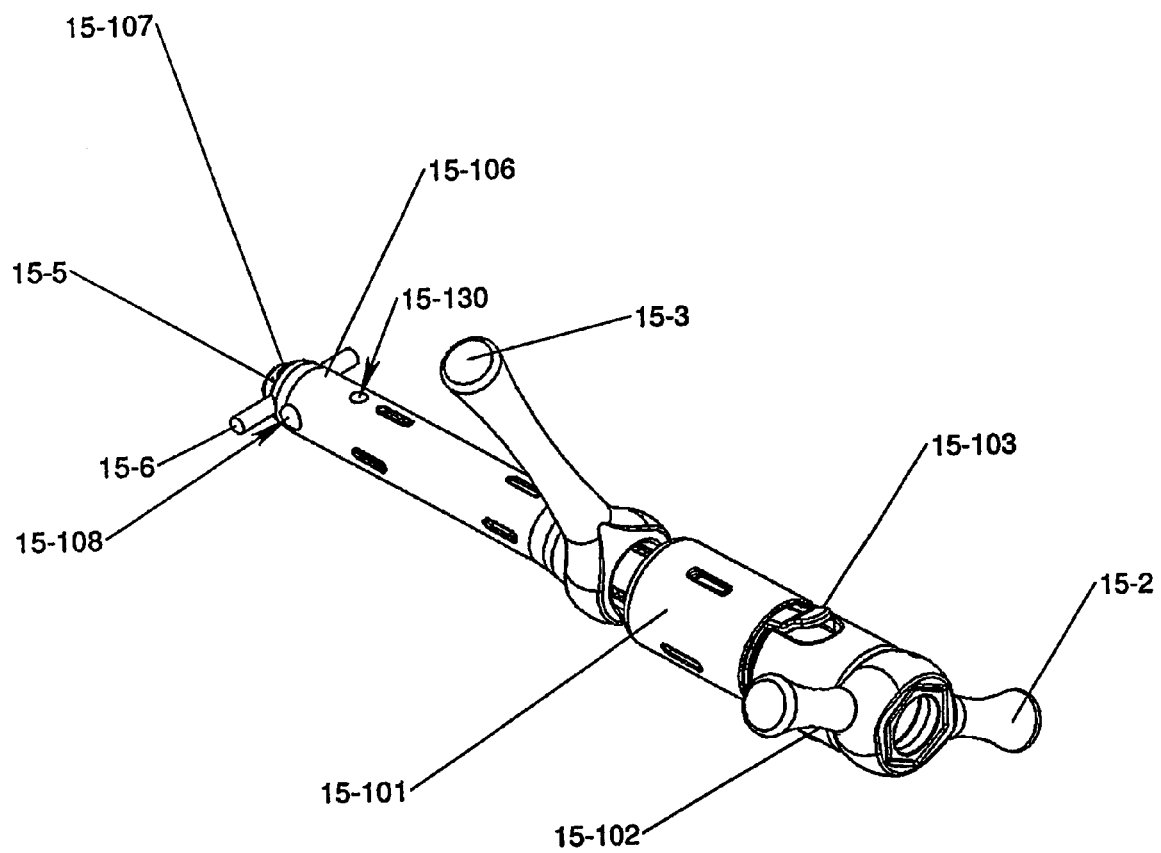
FIG. 15 is a perspective view of the reducer assembly, torque and counter handles in the rod engaged core and fully seated position.

Referring to FIG. 15, the reducer assembly, and torque and counter torque handles are shown with rod reduction complete. The rod 15-6 has been shifted by the outer shaft member 15-106 so that the rod 15-6 is fully seated within the tulip assembly 15-5.

Typically, the counter torque handle 15-3 would be required to complete the reduction procedure. As shown in FIG. 15, the counter torque handle 15-3 has been secured to the counter torque handle hexagonal shaped nut attachment structure 4-105. The jaw 2-31 of the counter torque handle 15-3 is slid into position onto the nut attachment structure 4-105 and locked into place via an internal flange of the counter torque handle jaw that engages the hexagonal shaped attachment structure 4-108. Note that the counter torque handle can be readily disconnected and reconnected to the reducer assembly 2-1 in different orientations with respect to the reducer assembly to allow ambidextrous functionality.

The counter torque handle 15-3 secures the reducer/inserter apparatus and provides counter torque when significant torque is applied to the torque handle 15-2 by the operator. Without the counter torque handle 15-3, the reducer/inserter apparatus would tend to twist and disengage from the tulip assembly 15-5 due to the high levels of torque applied by the operator to the torque handle.

Figure 16:
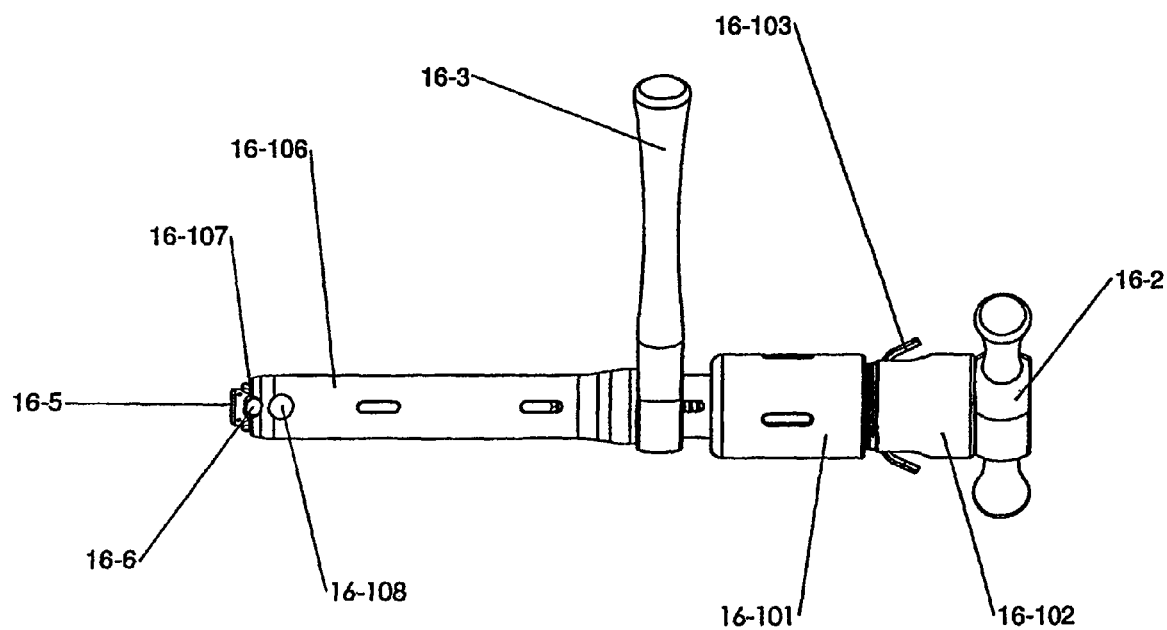
FIG. 16 is a front elevational view of the reducer assembly, torque and counter torque handles in the rod engaged core and fully seated position.
Figure 17:
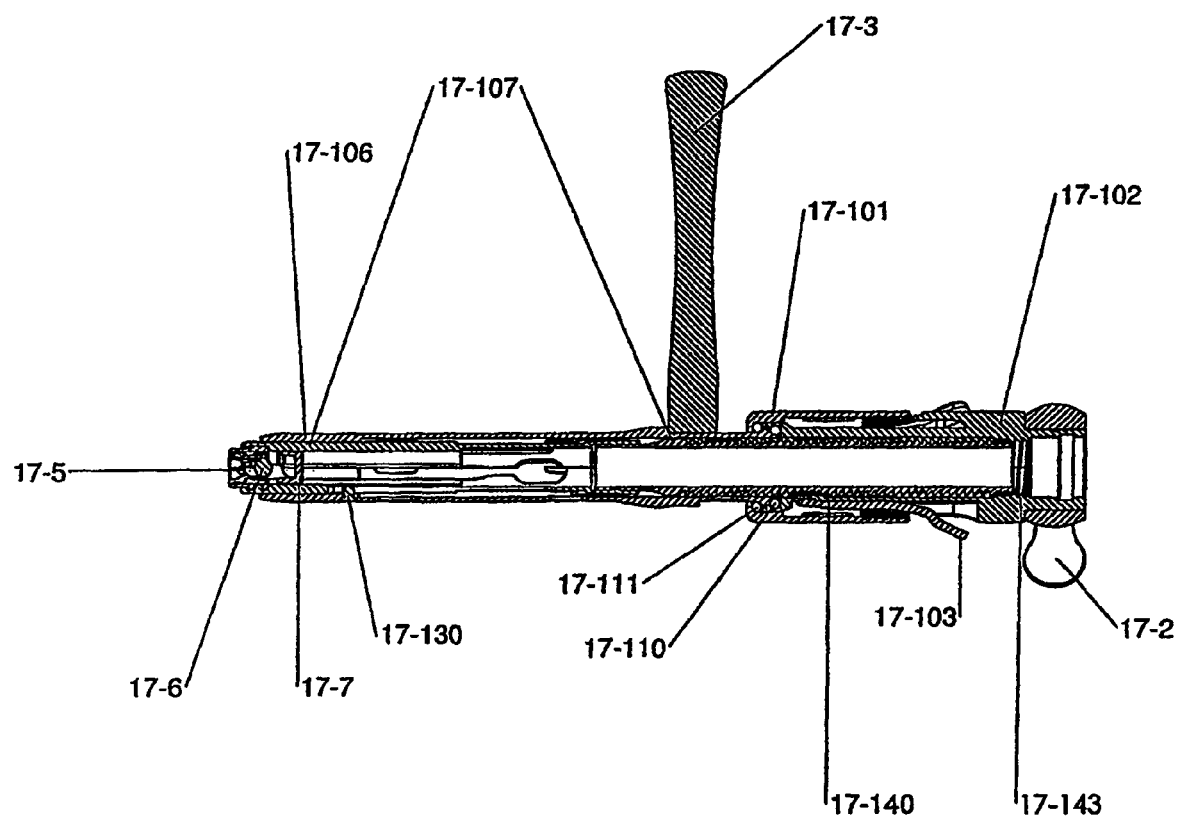
FIG. 17 is a front sectional view of the reducer assembly, torque and counter torque handles in the rod engaged core and fully seated position.

As shown in FIG. 16, the reducer assembly is in the fully reduced configuration with the rod 16-6 fully seated in the tulip assembly 16-5 and the inner shaft assembly 16-107 nearly completely retracted out of view after shifting up within the outer shaft member 16-106. The retraction of the inner shaft assembly 17-107 into the outer shaft member 17-106 is further illustrated in the cross-sectional view of FIG. 17. FIG. 17 illustrates that the inner shaft assembly 17-107 has now shifted with respect to the outer shaft member 17-106 and drive housing 17-102 so that the proximal end of the inner shaft assembly is situated at reference point 17-143, located near the proximal end of the instrument.

When the rod reduction is complete and the spinal rod 17-6 has entered the tulip member 17-5, the cap 17-7 (shown in position only for illustration purposes) then can be inserted into the tulip member 17-5.

Figure 18:
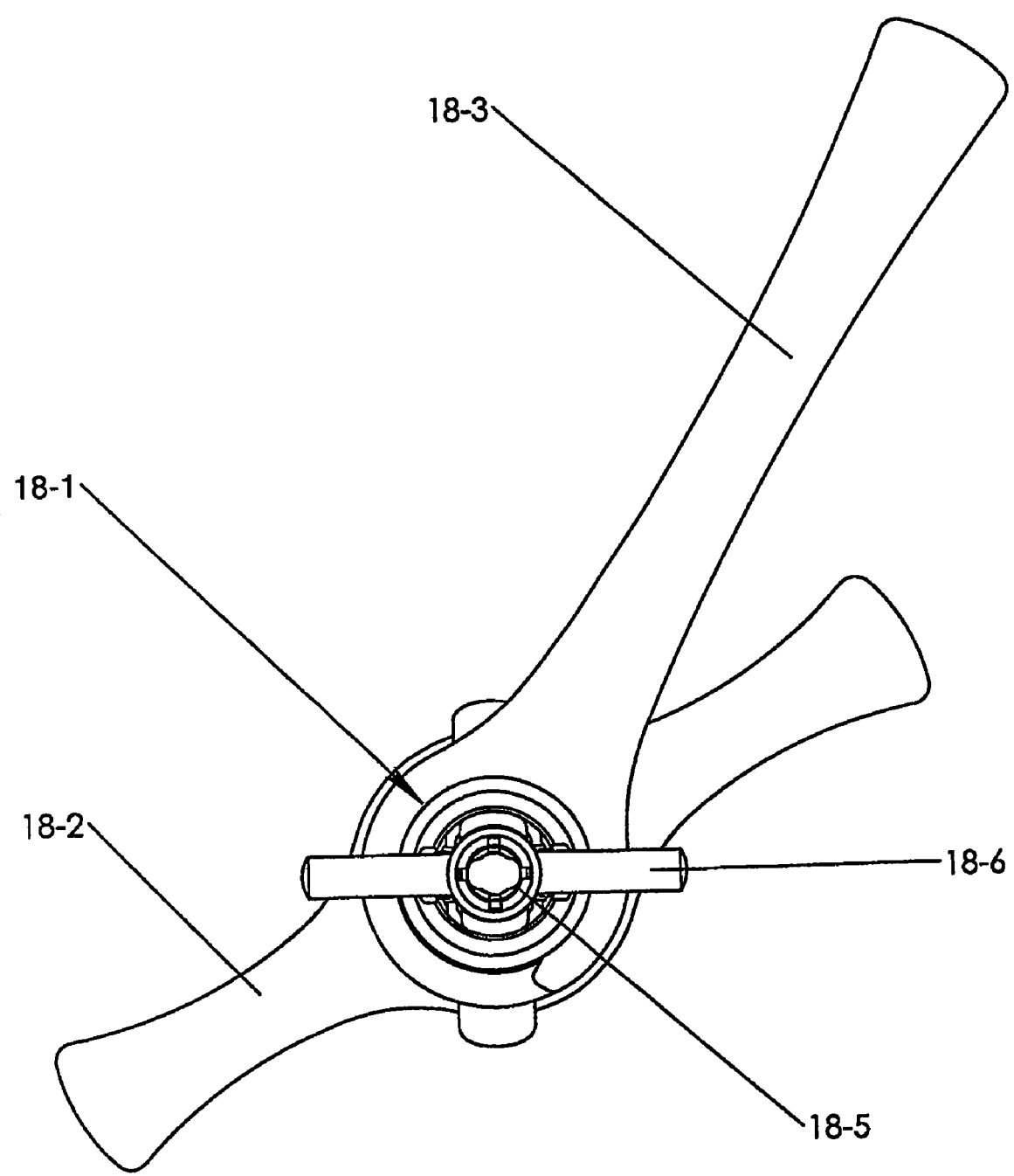
FIG. 18 is a side elevational view of the reducer assembly, torque and counter torque handles in the rod engaged core and fully seated position.

A view of the instrument along its axis from the proximal end is shown in FIG. 18. The circular profile of the reducer assembly 18-1 is compact and minimal relative to the circular profile of the tulip member 18-5, the spinal rod 18-6, and the torque and counter torque handles (18-2 and 18-3 respectively). In alternative embodiments (not shown), the cross-sectional profile of the reducer assembly 18-1 can have other shapes such as hexagonal or rectangular profiles. For example, the reducer assembly 18-1 could easily have a hexagonal profile that would still allow the components to shift over one another.

Figure 19:
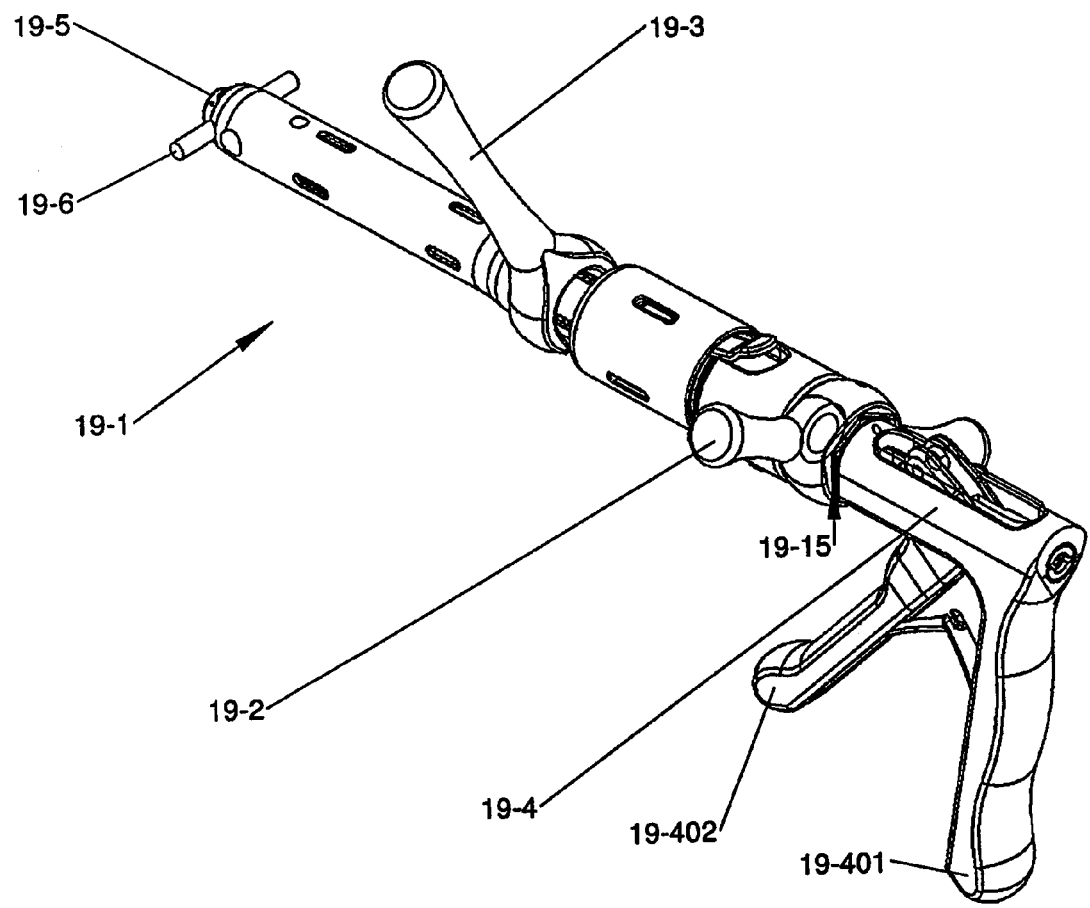
FIG. 19 is a perspective view of the complete reducer and cap inserter assembly in the cap engaging tulip position.

Referring to FIG. 19, the reducer assembly 19-1 is shown assembled with the cap inserter assembly 19-4 in an isometric view with the cap inserter assembly locked in position. The cap inserter assembly 19-4 is inserted axially into the throughbore 19-15 of the reducer assembly 19-1 so that a cap held by the distal end of the cap inserter 19-4 is shifted through the throughbore 19-15 and into alignment with the tulip assembly 19-5 and spinal rod 19-6 held in the fully reduced position at the distal end of the reducer assembly 19-1.

Figure 20:
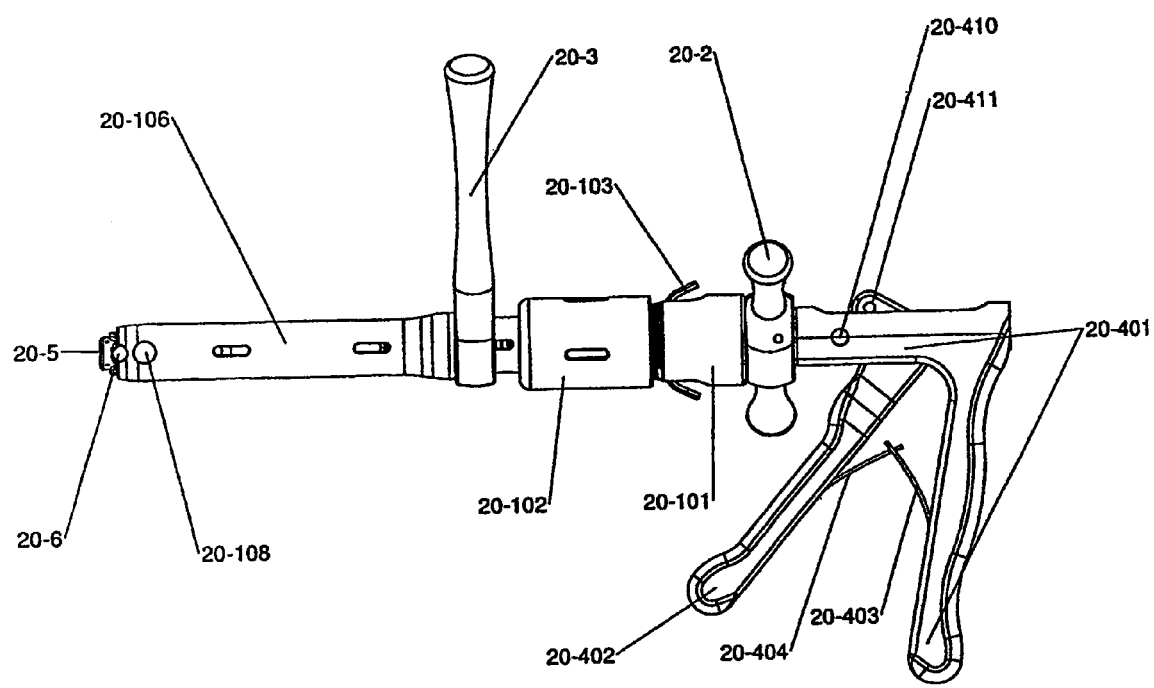
FIG. 20 is a front elevational view of the complete reducer and cap inserter assembly in the cap engaging tulip position.

As shown in FIG. 20, the cap inserter actuator 20-402 is pivotally connected to the cap inserter handle 20-401. The cap inserter actuator 20-402 is pivoted toward the cap inserter handle 20-401 to advance the cap 17-7 into the tulip member 17-5. Springs 20-403 and 20-404 bias the actuator 20-402 away from the insert handle 20-401. When the operator releases the cap inserter actuator 20-402, the handle flat spring 20-403 and the actuator flat spring 20-404 restore the cap inserter actuator 20-402 to its original position.

The handle flat spring 22-403 is connected to the cap inserter handle 22-401 within a recess in the cap inserter handle 22-401 and secured with a handle spring screw 22-405. The handle flat spring 22-403 interlocks with the actuator flat spring 21-404, which is secured by a similar arrangement to the cap inserter actuator 22-402.

Figure 21:
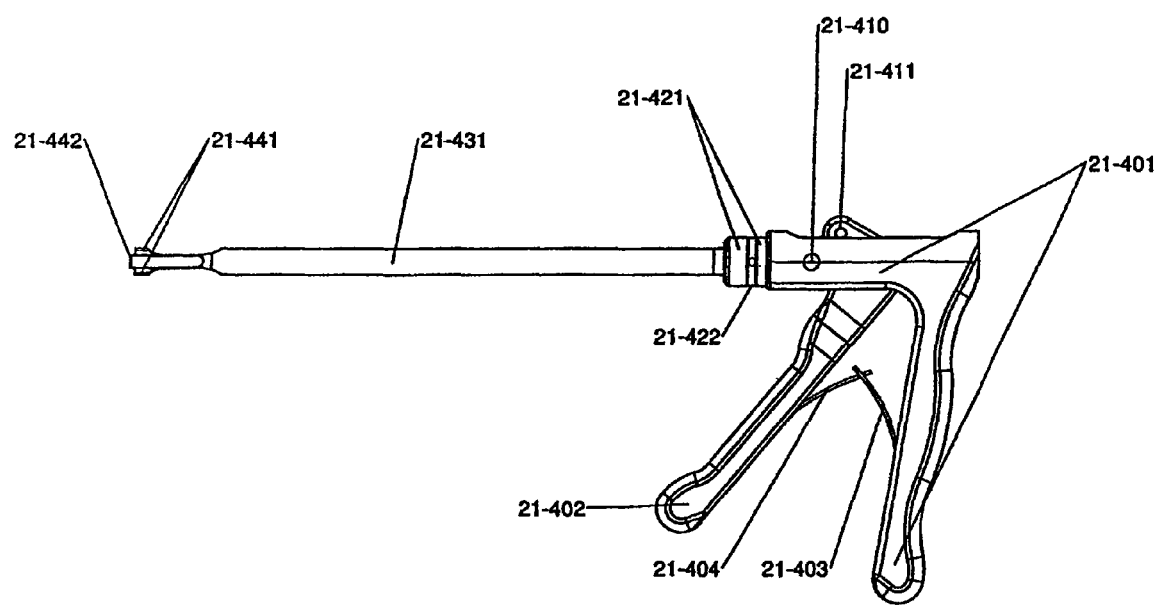
FIG. 21 is a front elevational view of the cap inserter assembly.

The cap inserter assembly 2-4 is shown in FIG. 21 isolated from the mechanical elements of the reducer assembly 2-1. The actuator 21-402 is operably coupled to a drive member 21-431 that shifts axially in response to pivoting of the actuator 21-402. The drive member 21-431 has a head portion 21-442 with arms 21-441 for holding the cap of the tulip assembly.

The cap inserter assembly 2-4 further includes a quick connect locking mechanism 22-422 which is housed in the locking structure 22-421. The quick connect locking mechanism 22-422 allows the cap inserter assembly to lock into place into the reducer assembly 2-1 when the cap inserter drive member 22-431 has been inserted into the throughbore 2-15 of the reducer assembly 2-1. Once the operator pivots the cap inserter actuator 22-402, then the locking mechanism 22-422 expands radially to lock into a locking groove or recess of the reducer member 2-1, holding the body of the inserter in place relative to the reducer and allowing the drive member 22-431 to shift the cap 3-5 distally and into engagement with the tulip assembly. The cap inserter assembly 2-4 is disconnected from the reducer assembly 2-1 by the operator simply releasing the cap inserter actuator 22-402. The exact function of the locking mechanism 22-422 will be explained in further detail in the detailed description for FIGS. 25 and 26.

Figure 22:
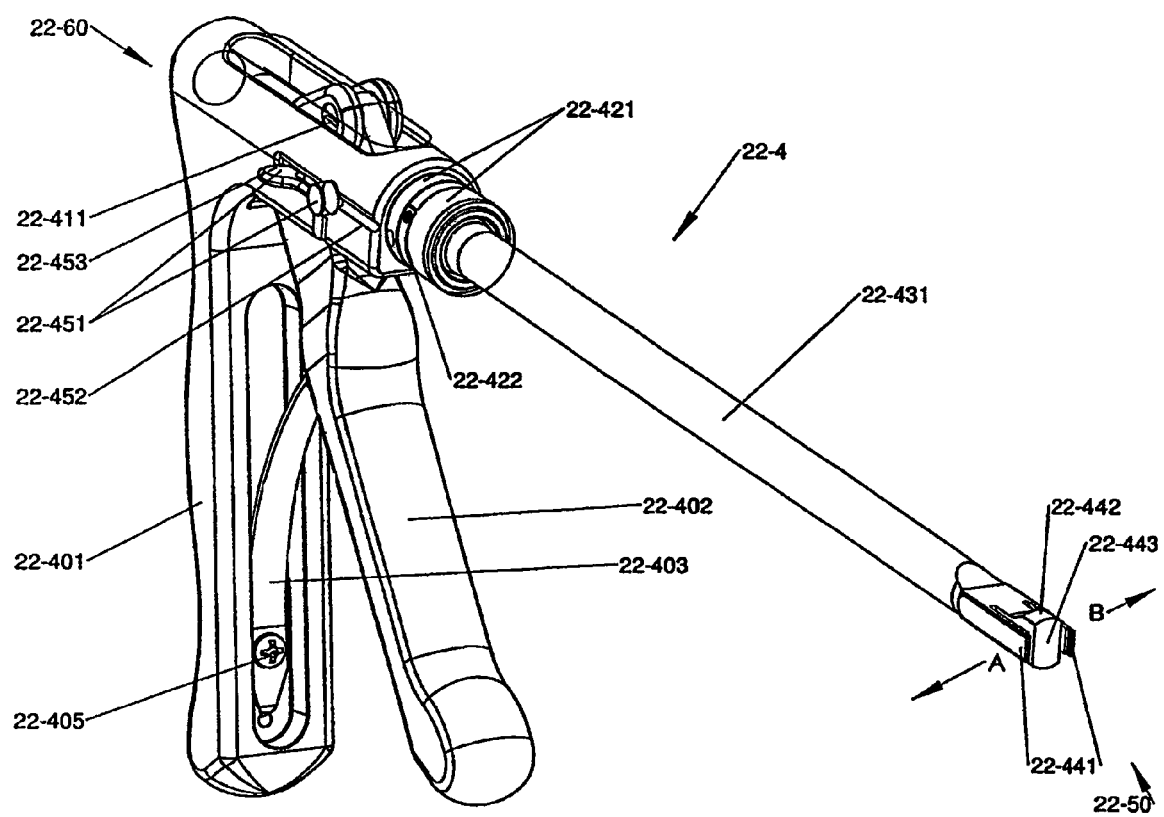
FIG. 22 is a perspective view of the cap inserter assembly.

The insert assembly 22-4 may also include a selector switch 22-451, as shown in FIG. 22 in a partial lock position, to limit shifting of the drive member 22-431 so that the cap attached thereto is inserted into the tulip assembly only to a provisional lock position, keep the operator from fully locking the cap 17-7 into tulip member 17-5 and thus allowing some adjustment of the spinal rod 17-6. Shifting the selector switch 22-451 to a full lock position allows the cap 17-7 to fully lock into the tulip member 17-5. In the embodiment shown in FIG. 22, the selector switch 22-451 has a lever 22-453 that is shifted proximally 22-60 to the pivotal lock position to limit movement of the drive member 22-431. Shifting the switch distally 22-50 to the full lock position thereafter enables full locking of the cap. A groove 22-452 provides a detent to hold the switch lever 22-453 in the selected direction. The switch lever 22-453 is slightly flexible so that it can bend or shift slightly in a direction parallel to the axis about which it pivots, allowing it to ride along the exterior of the instrument. When the switch lever is pivoted so that it reaches the groove 22-453 the lever resiliently deflects into the groove and is held therein until sufficient angular force is applied to the level to push it out of the groove. The sides of the groove 22-452 are ramped to cause deflection of the lever when sufficient pivoting force is applied, eliminating the need to manually pull the lever out of the groove and away from the instrument surface prior to pivoting.

At the distal end 22-50 of the cap inserter assembly 22-4, the radial cap attachment arms 22-441 can be seen. The cap attachment arms 22-441 resiliently deflect in the A and B directions to snap-lock around the cap member. The drive member head portion 22-442 has a flat drive face 22-443 provides the bearing surface for the pushing drive member 22-431 when force is applied to lock the cap 17-7 in place on the tulip member 17-5.

Figure 23:
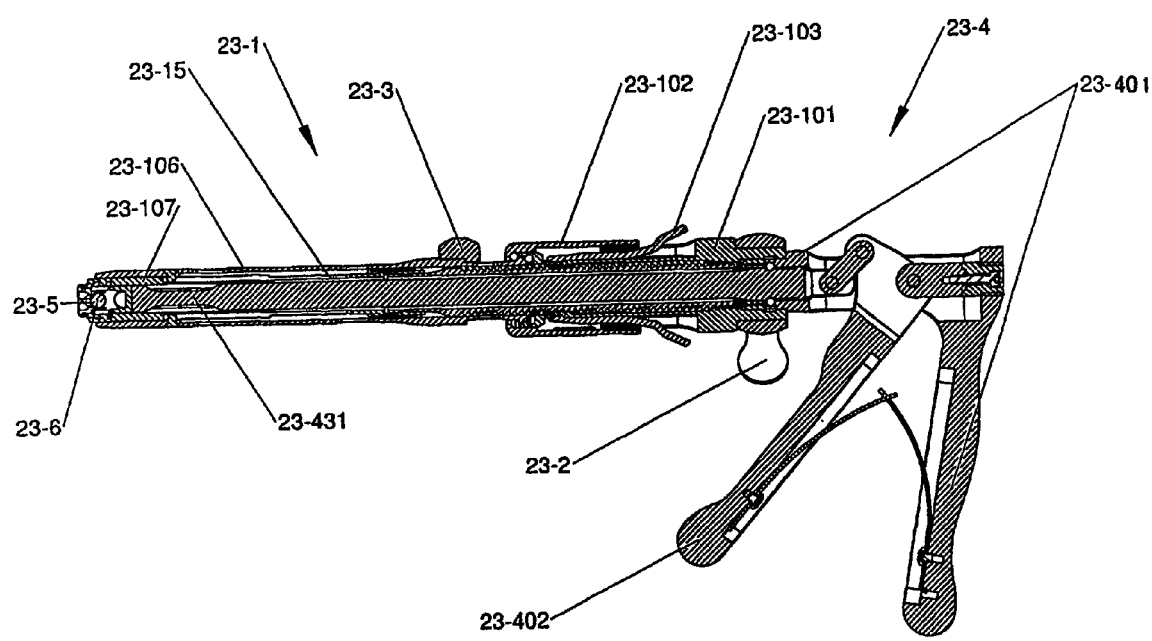
FIG. 23 is a front sectional view of the complete reducer and cap inserter assembly in the cap engaging tulip position.

Referring to FIG. 23, the reducer assembled with the cap inserter assembly is shown with the driving member 23-431 extending axially along the reducer member throughbore 23-15 along most of the length of the reducer assembly 23-1.

Figure 24:
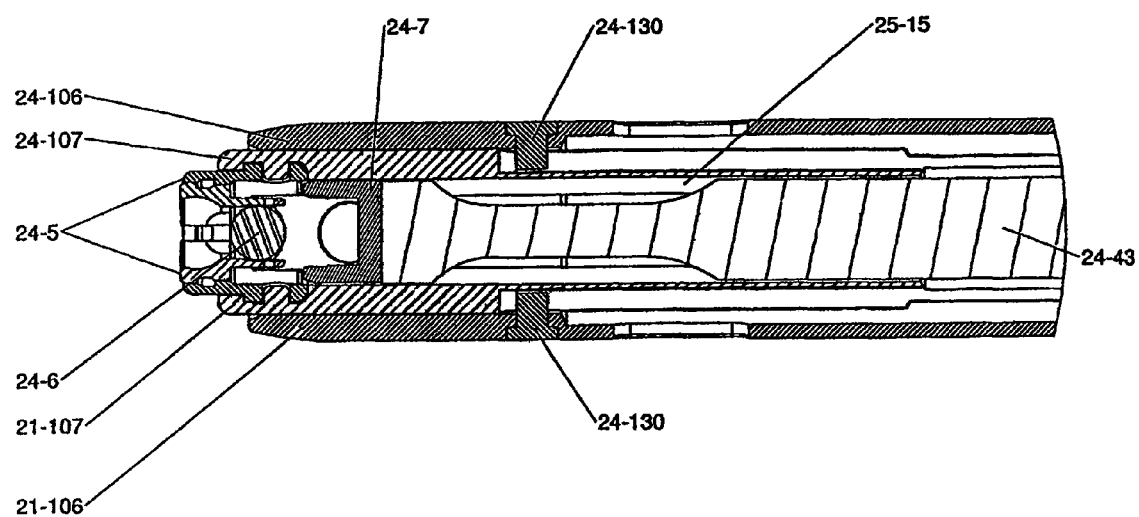
FIG. 24 is a detailed front sectional view of the distal end of the complete reducer and cap inserter assembly in the cap engaging tulip position.

In the detailed sectional view of the distal end of the inserter assembly of FIG. 24, the cap 24-7 is positioned ready to be locked into the tulip member 24-5. The drive member 24-431 holds the cap 24-7 and the drive member and cap are constrained by the walls of the inner shaft assembly 24-107 to drive the cap 24-7 axially through the reducer member throughbore 24-15. The constraint of the walls of the inner shaft assembly 24-107 assures that the cap 24-7 will be inserted correctly into the tulip member 24-5 and not slip out of position during the application of force to the drive member via the actuator 23-402.

Figure 25:
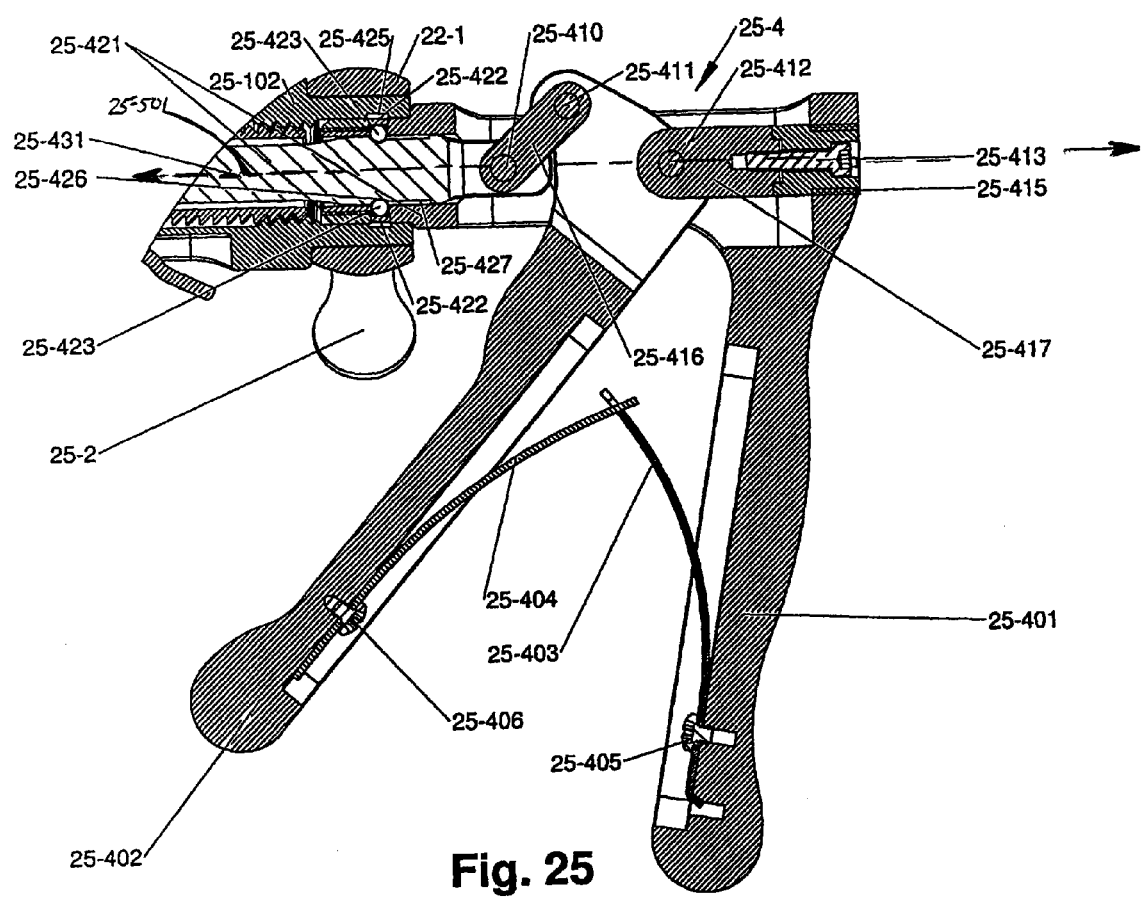
FIG. 25 is a detailed front sectional view of the proximal end of the complete reducer and cap inserter assembly in the cap engaging tulip position.

The proximal end of the cap inserter is shown in the cross-sectional view of FIG. 25. In the illustrated embodiment, a fixed actuator pivot pin 25-412 is fixed to handle housing 25-401 provides a pivot shaft around which the actuator lever 25-402 pivots when shifted between opened and closed positions thereof.

The relationship between the actuator pin 25-412 and an actuator linkage pin 25-411 coupled to the transverse projecting portion at the other side of the cap inserter actuator 25-402 provides the first link in a three bar linkage that provides the leverage to apply the force necessary to lock the cap 24-7 to the tulip member 24-5 shown in the previous drawing in FIG. 24. The actuator linkage pin 25-411 is further pivotably coupled to one end of a linkage member 25-416, which is also pivotably coupled at its other end to the drive member 25-431 through a drive pivot pin 25-410. The pivoting motion of the cap inserter actuator 28-402 will cause the actuator linkage pin 28-411 to pivot about the pins 25-410 and 25-411 and shift the link member 25-416 from extending obliquely to the tool axis 25-501 to be generally aligned therewith, which will in turn translate to shifting of the drive pin 25-410 and drive member 25-431. The actuator and associated linkages may be configured to deliver a desired amount of force to the cap, such as about 400-2000 pounds, through the drive member.

In addition, the mechanical components that allow for the quick connection of the entire cap inserter apparatus 25-4 to the reducer assembly 25-1 can be seen in FIG. 25. The locking mechanism 25-422 is carried by and generally fits within the locking structure 25-421 of the cap inserter assembly 25-4 and the rod reducer assembly 25-1. In the preferred embodiment, the locking mechanism 25-422 is a ring or collar of a configuration and/or material that allows it to expand radially outward into an interior annular recess 25-425 in the drive housing structure 25-102. In order to allow for expansion, the collar may have one or more slits therein. The locking mechanism 25-422 is driven into the recess of the drive housing structure 25-102 when the cap inserter actuator 25-402 advances the drive member 25-431 which shifts shiftable elements 25-423 radially outward as they ride on a radially wider surface portion 25-427 of the drive member 25-431. The shiftable elements 25-423 move transversely, and more specifically orthogonally, relative to the axial shifting direction of the drive member 25-431, which then forces the ring or collar of the locking mechanism 25-422 extending about the elements into mechanical interference with the drive housing structure 25-102, thus locking the cap inserter assembly 22-4, and specifically the locking housing 25-421 thereof, to the rod reducer assembly 22-1 together.

When the actuator 25-402 is pivoted away from the handle 25-401 to the open position, the shiftable elements 25-423 rest in proximal radial recesses 25-425 of the drive shaft member 25-431 so that the locking mechanism 25-422 adjacent to the shiftable elements is in a radially contracted position that does not interfere with the rod reducer assembly. As the drive member 25-431 shifts axially, when the actuator 25-402 is pivoted, the shiftable elements 25-423 of the lock mechanism are cammed out of the drive member recesses 25-425 and ride on the axially wider cam surface portion 25-427 of the drive member 25-431. Riding on the wider locking portion 25-427 orients, shiftable elements 25-423 radially outward, in turn thereby radially pushing or expanding the locking mechanism collar 25-422 radially outward into the reducer assembly annular recess 25-425, locking the cap inserter 25-4 in place within the rod reducer assembly, so that force exerted by the drive member is directed axially toward the distal end of the reducer assembly instead of causing the inserter 25-4 to back out of the reducer.

Alternative locking mechanisms may be provided, or the locking mechanism may be omitted altogether. In alternative embodiments, the cap inserter actuator 20-402 also could have other types of mechanisms to mechanically transmit force. For example, the cap inserter actuator 20-402 can be a threaded drive system similar to that of the reducer assembly 18-1, or a ratchet system. Finally, in another embodiment a power source could be used to advance the drive member, such as an electric motor, hydraulic or pneumatic motor.

Figure 26:
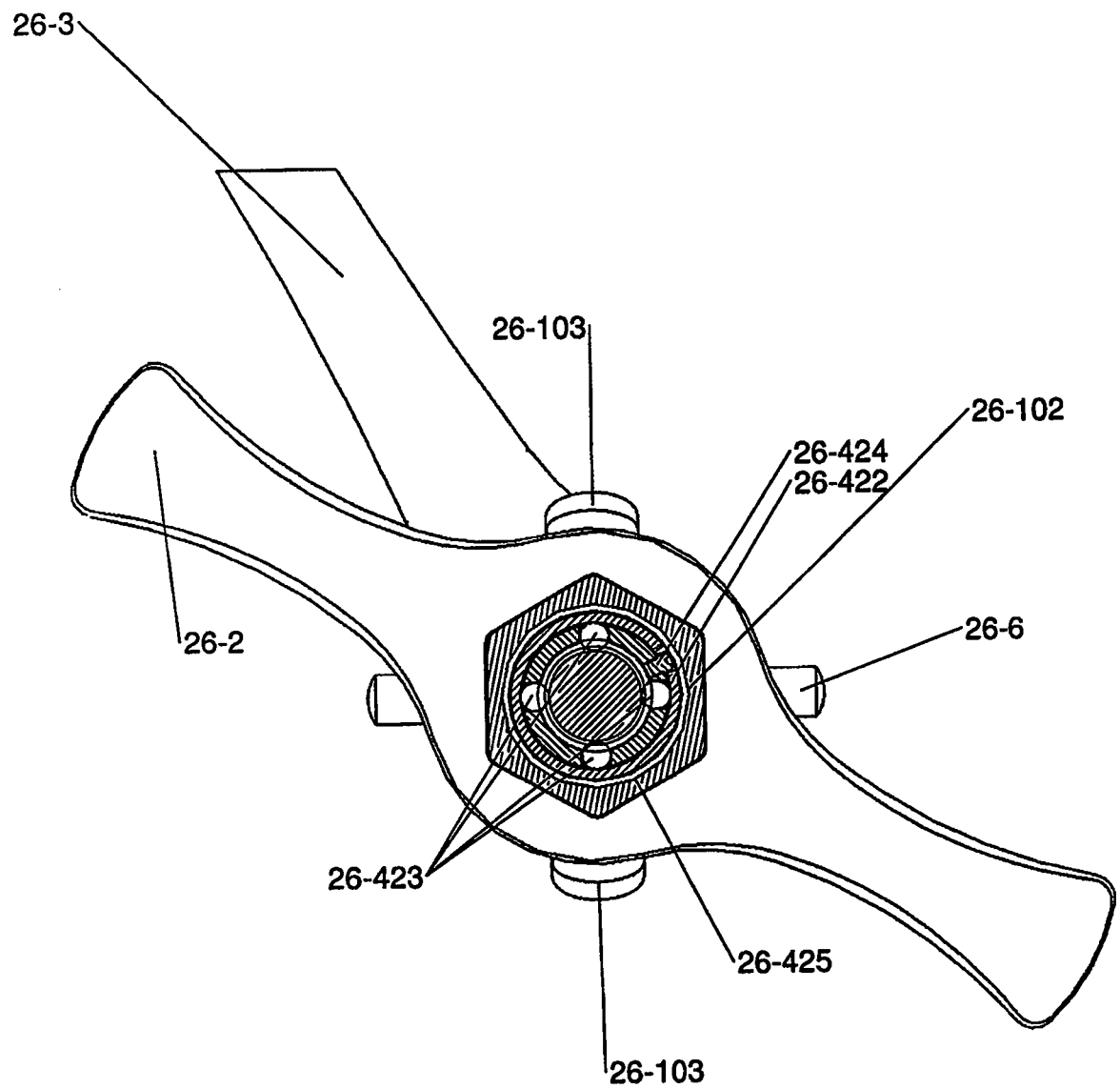
FIG. 26 is a side sectional view of the complete reducer and cap inserter assembly in the cap engaging tulip position.

Referring to FIG. 26, the reducer and cap inserter assembly is shown in cross section from the proximal end of the assemblies with the locking mechanism for the quick connect visible together with the interaction of the mechanical components that allow for the quick connection function as described relative to FIG. 25.

As previously explained, the quick connecting locking mechanism 25-422 is locked to the drive housing structure 26-102 by radial movement of shiftable elements 26-423, which in turn cause expansion of the collar locking mechanism 26-422 into the annular recess 26-425. As shown in FIG. 26, a post member 26-424 keeps the ring or collar of the locking mechanism 25-422 from rotating. Migration of the ring or collar of the locking mechanism 25-422 through rotation may cause the unlocking of the reducer and cap inserter assemblies (2-1 and 2-4 respectively) from each other when the cap inserter actuator 25-402 is released by the operator, such as could occur if any of the shiftable elements 26-423 entered the slit in the collar keeping the collar from properly contracting.

In alternative embodiments, the quick connect mechanism could be supplemented or replaced with other types of locking mechanisms. For example, a set screw could be used to lock the cap inserter assembly 2-4 into the reducer assembly 2-1. Also, the cap inserter assembly 2-4 could lock into the reducer assembly 2-1 with a threaded, bayonet, cam locking, or other connection.

The cap inserter may also be provided with a fine tune mechanism, such as 25-413 shown in FIG. 25, to adjust the positioning of the drive member 25-431. The fine tune mechanism 25-413 allows for adjustment of the position of the actuator pin 25-412. The fine tune mechanism 25-413 may be adjusted with a simple screw driver. The fine tune mechanism 25-413 controls the position of the actuator pin 25-412 through adjusting the position of the actuator support structure 25-417. The actuator support structure 25-417 establishes the axial position of the cap inserter actuator 28-402, within the cap locker and pivotably couples the actuator 95-402 to the cap locker through the actuator pin 25-412. Fine tuning of the position of the actuator pin 25-412 may be desirable due to the manufacturing tolerance of the components of the reducer/inserter apparatus. The fine tune mechanism 25-413 provides a means to compensate for this error and assures the correct placement of the actuator pin 25-412 once all of the parts of the apparatus have been assembled in the factory so that the drive member 25-431 applies the desired amount of force to the cap.

A connection member 25-415 attaches the fine tune mechanism 25-413 to the reducer/inserter apparatus. The illustrated connection member 25-415 is threaded and screws into the cap inserter handle 25-401, with the fine tune mechanism 25-413. Therefore, after the reducer/inserter apparatus has been assembled, the connection member 25-415 and fine tune mechanism 25-413 can then be adjusted as the final step in assembly of the apparatus.

Figure 27:
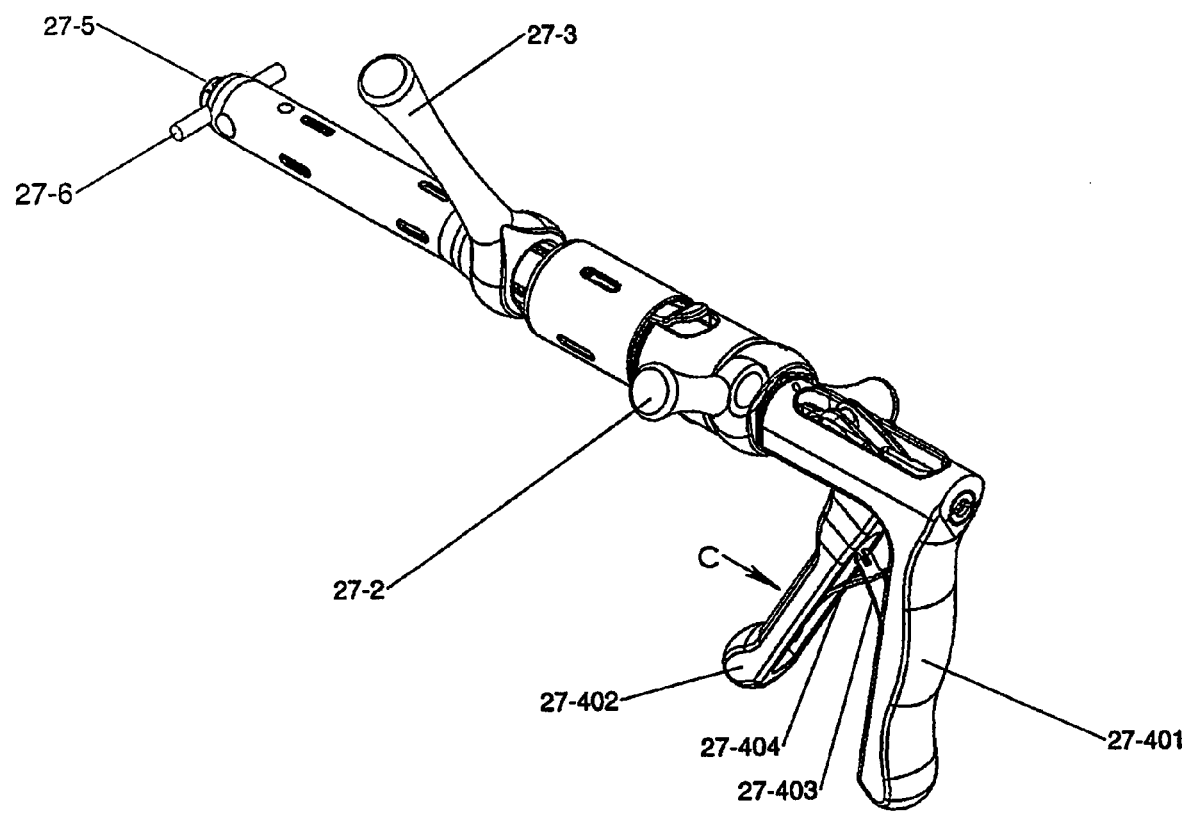
FIG. 27 is a perspective view of the complete reducer and cap inserter assembly in the cap seated to initial position.

Referring to FIG. 27, when the cap inserter actuator 27-402 is squeezed by the surgeon, applying force in direction C, the cap 24-7 is driven axially into the tulip member 27-5. If the selector switch is in the partial or provisional lock position, the cap is driven only to a provisional lock position. The provisional lock of the cap 24-7 allows the surgeon to secure the cap 24-7 into the tulip member 27-5 yet allows the surgeon to still make adjustments to the position of the spinal rod 27-6. The displacement of the cap inserter actuator 27-402 can be best seen by comparing FIG. 19 to FIG. 27. Typically, the cap inserter actuator 27-402 will be initially depressed with the selector lever in the on or provisional lock position to allow the cap 24-7 to be seated or releasably locked in the provisional position in the tulip member 24-5. FIG. 28 shows the cap inserter actuator 27-402 pivoted so that the cap 28-7 is provisionally locked to the tulip assembly 28-5.

As shown in FIG. 28, pivoting the cap inserter actuator 28-402 in the C direction causes the actuator linkage pin 28-411 to move in the D direction, which in turn shifts linkage 28-416 and drives the drive member 28-431 in the desired distal axial direction E.

Figure 29:
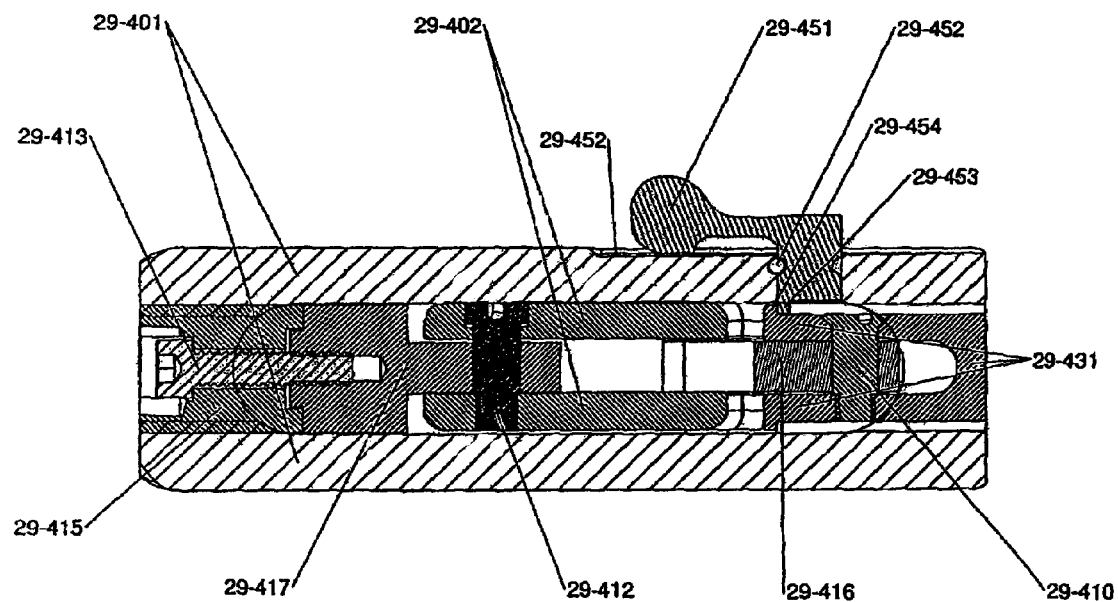
FIG. 29 is a detailed bottom sectional view of the cap inserter assembly in the cap seated to initial position.

Referring to FIG. 29, the selector switch 29-451 is mechanically coupled to the cap inserter handle 29-401 with a retention pin 29-452. The retention pin 29-452 is driven into the cap inserter handle 29-401 and into an annular recess of the selector switch. The retention pin 29-452 may be laser welded at both ends of the safety column 29-452 or otherwise fixed to the handle 29-401, and holds the selector switch to the handle as it is rotated.

The selector switch 29-451 is shown in the provisional position in FIG. 29 to keep the drive member 29-431 from fully traveling in the distal direction which is toward the right in FIG. 29 (unlike the other drawings). An abutment portion 29-453 extends radially inward and is positioned toward the proximal end of the instrument with the selector switch 29-451 in the provisional lock position, interfering with abutment flange 29-454 on the drive member to stop linear movement of the drive member when shifted into engagement with the switch abutment portion 29-453. However, when the selector switch 29-451 is rotated 180 degrees then the abutment portion 29-453 on the safety actuator 29-451 is rotated toward the distal end of the switch to the full lock position, allowing the drive member 29-431 to move further distally without the drive member abutment flange 29-454 abutting the selected switch abutment portion 29-453. When the drive member 29-431 can fully travel until the flange 29-454 thereof engages the switch portion 29-453 shifted in the full lock position then the cap 28-7 will be fully inserted into the tulip member 28-5 for the final locking of the fixation system.

The arrangement of the other mechanical elements for the drive system of the cap inserter assembly 2-4 are also shown in FIG. 29. The fine tune mechanism 29-413 controls the placement of the actuator pin 29-412 through the actuator support structure 29-417 as previously described. The actuator pin 29-412 then connects and transmits the force applied by the operator from the cap inserter actuator 29-402 eventually to the drive member 29-431.

Figure 30:
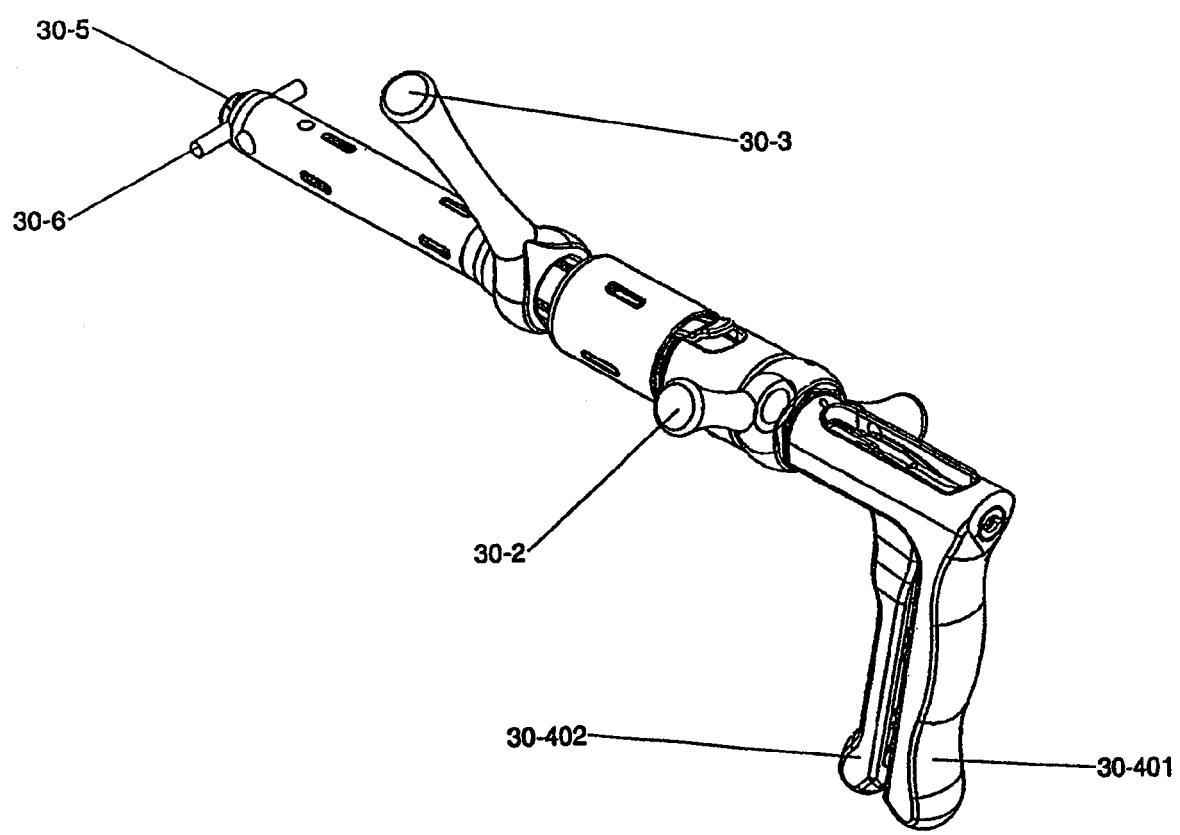
FIG. 30 is a perspective view of the complete reducer and cap inserter assembly in the cap fully seated position.

Referring to FIG. 30, the complete reducer and cap inserter assembly is shown with the reduction and insertion procedure completed in the full cap locking position. The apparatus is shown after the reduction and provisional cap locking procedures have been completed. Note that all subsequent drawings show only the final state after the procedures have been completed.

In the preferred embodiment, the selector switch 22-451 is in the full locking position to allow the operator to fully lock the cap 28-7 into tulip member 30-5 by fully pivoting the cap inserter actuator 30-402 toward the handle 30-401. The full locking of the cap 28-7 secures the cap 28-7 into the tulip member 28-5 so that the spinal rod 30-6 is immobilized with respect to the tulip assembly.

Figure 31:
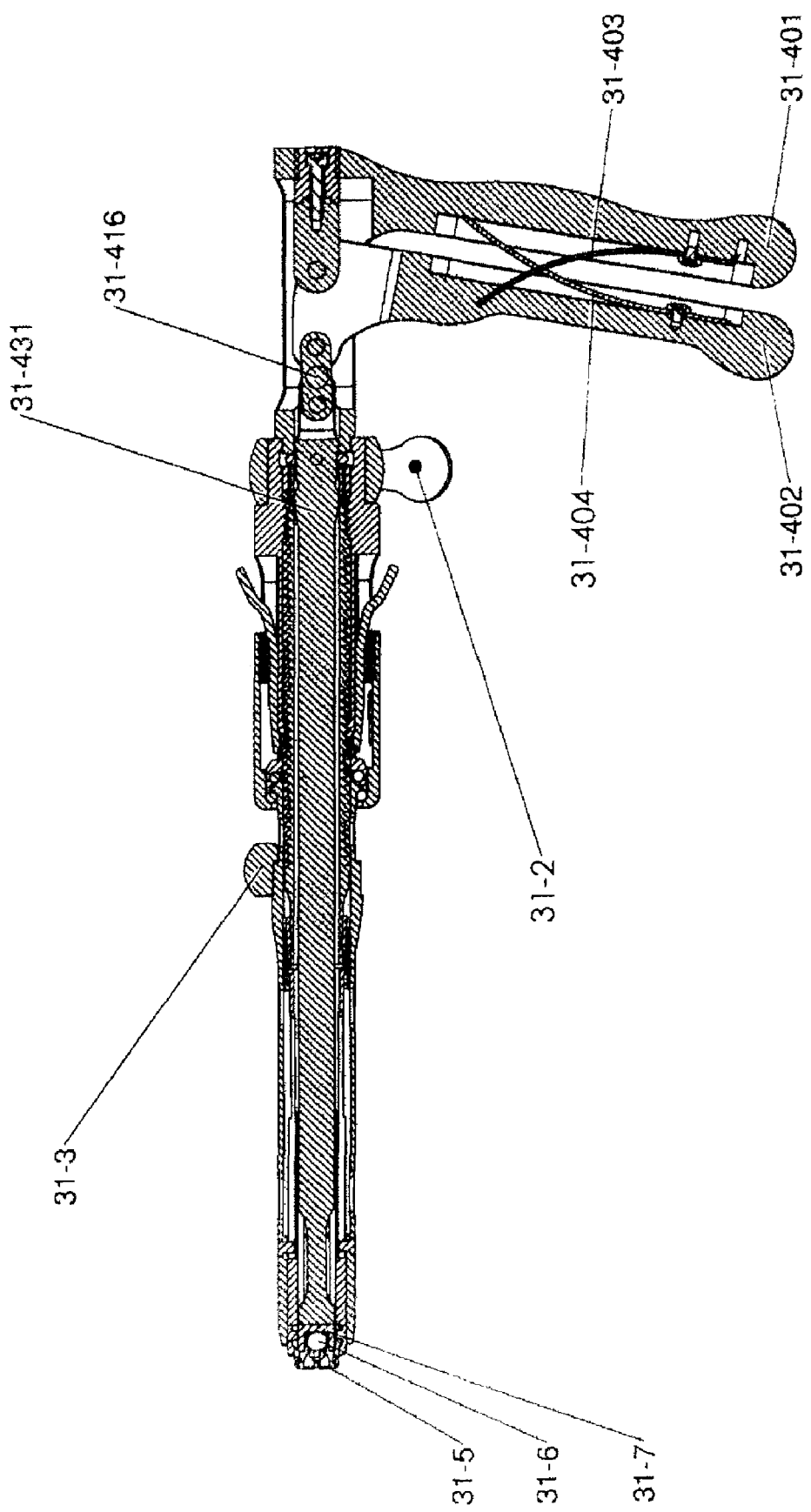
FIG. 31 is a front sectional view of the complete reducer and cap inserter assembly in the cap fully seated position.

Referring to FIG. 31, the drive member 31-431 is extended to the furthest most distal position, and the cap 31-7 has entered and fully locked into the tulip member 31-5. All of the mechanical linkages of the cap inserter assembly such as the linkage member 31-416 and the cap inserter actuator 31-402 have achieved a linear arrangement in the distal direction.

Figure 32:
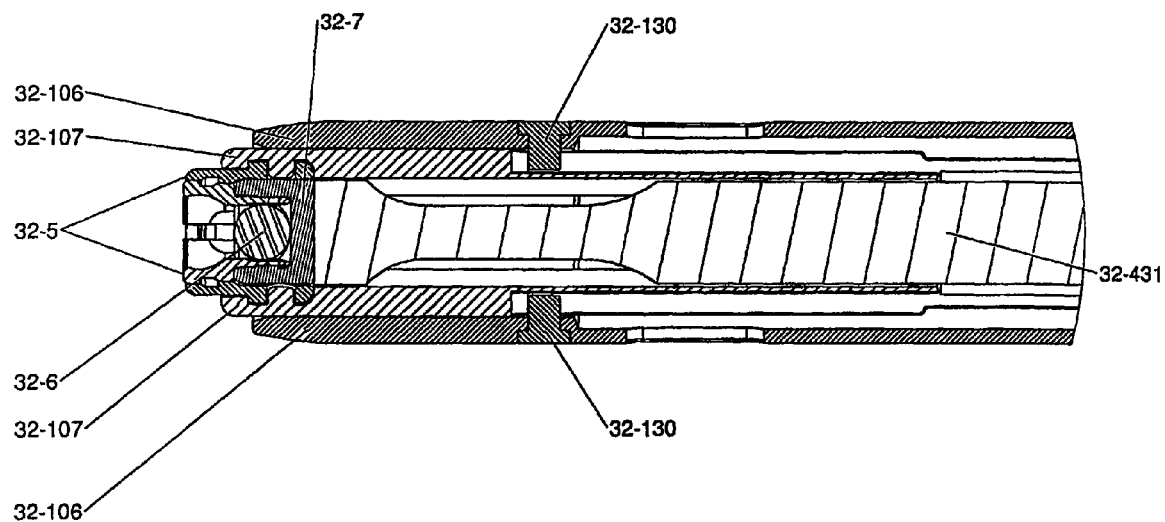
FIG. 32 is a detailed front sectional view of the distal end of the complete reducer and cap inserter assembly in the cap fully seated position.

The full locking of the cap is shown further in FIG. 32. The cap 32-7 has been fully inserted into the tulip member 32-5 applying a radial locking force onto the rod 32-6 and completing the assembly of the fixation system. The spinal rod 32-6 is thereby fixed between the cap 32-7 and tulip member 32-5.

Material Components for the Reducer/Inserter Apparatus:

The reducer/inserter apparatus can be made from any suitable, structurally strong material. The structural support portion and other components, such as the projections, are constructed of suitable materials which are compatible with the uses and environments into which the device will be utilized. Preferably, the reducer/inserter apparatus, especially the exterior components, is constructed of metallic materials such as 17-4 Stainless steel, and 465 stainless steel. Alternatively, the exterior components can be made of other metal alloys such as titanium.

In some embodiments, the reducer/inserter apparatus can be made from non-conductive material such as various plastics, such as polyetheretherketone (PEEK) and related compounds, in order to avoid conduction of electricity. In some other embodiments, the reducer/inserter apparatus can be made from ceramics that provide non-conductive characteristics. Finally, a composite of the previously discussed materials can be used that combine the properties of the said materials, i.e. metals combined with non-conductive materials. Coatings, such as chrome coatings, and lubricants may also be applied in order to reduce friction and otherwise enhance function of the instrument.

Reducer/Inserter Deployment Method or Procedure:

The method for operating the reducer/inserter apparatus begins with making a surgical incision, and distracting the tissue in place. The reducer assembly 2-1 is provided to the surgeon. The surgeon then positions the reducer assembly 2-1 into the incision.

The surgeon then operates the reducer assembly if necessary so that the inner shaft assembly 3-107 extends out from the bottom of the outer shaft member and connects the clamp portion of the inner shaft assembly of the reducer assembly 2-1 to the desired tulip member 3-5 while constraining a spinal rod 3-5 within the arms of the inner shaft assembly 3-107. The surgeon then fastens the desired tulip member 3-5 to the reducer assembly 2-1 by slightly retracting the inner shaft assembly 3-107 by either (a) rotating the drive cover 3-101 and drive housing structure 3-102; (b) depressing the tabs on the drive release mechanism 3-103, linearly shifting the inner shaft assembly 3-107, and then releasing the tabs; (c) compressing the drive cover 3-101 and drive housing structure 3-102 into the inner shaft assembly 3-107 with the internal ratcheting mechanism of the thread release mechanism 5-103; or (d) a combination thereof.

The surgeon then reduces the spinal rod 3-6 onto the tulip member 3-5, i.e. drives the spinal rod 3-6 into the yoke of the tulip member 3-5, by either (a) rotating the drive cover 3-101 and drive housing structure 3-102; or (b) depressing the tabs on the drive release mechanism 3-103, physically manipulating the inner shaft assembly 3-107, and then releasing the tabs; or (c) compressing the drive cover 3-101 and drive housing structure 3-102 into the inner shaft assembly 3-107 with the internal ratcheting mechanism of the thread release mechanism 5-103; or (d) a combination thereof. The surgeon may attach a torque handle 2-2 or counter torque handle 2-3 at any point of the procedure to assist in rotating the drive cover 3-101 and drive housing structure 3-102.

A cap 17-7 is attached to the distal end of the cap inserter assembly 2-4. The cap inserter assembly 2-4 is then inserted into the reducer assembly 2-1 by placing the cap inserter assembly 2-4 into the central throughbore 2-15 of the reducer assembly 2-1 with the cap 17-7 attached. The cap inserter assembly 2-4 is locked into the reducer assembly 2-1 to form one integrated apparatus.

The selector switch 22-451 is placed in the provisional locking position and the cap inserter actuator is shifted to drive the cap into the tulip to the provisional lock position, wherein some adjustment of the rod is allowed. The selector switch 22-451 is then placed in the full lock position and the cap inserter actuator is shifted to drive the cap fully into the tulip to the final lock position, immobilizing the rod with respect to the tulip assembly. The surgical site is then closed and the procedure is complete.

It is intended for the following claims to cover these and any other departures from the disclosed embodiment which fall within the true spirit of the invention.

What is claimed is:

1. A method for securing a spinal rod to a vertebra, the method comprising:
   securing a fixation device and a coupling device to the vertebra;
   securing a rod reducing assembly to the coupling device so that the spinal rod is positioned between the coupling device and a reducing member of the rod reducing assembly;
   disengaging a drive mechanism for the rod reducing member with the rod reducing assembly secured to the coupling device;
   shifting the reducing member into contact with the spinal rod without operation of the drive mechanism;
   engaging the drive mechanism for driving the reducing member;
   operating the drive mechanism to apply force to the reducing member to shift the spinal rod into the coupling device; and
   driving a cap member into locking engagement with the coupling device after the reducing member has shifted the rod into the coupling device;
   wherein the step of engaging the drive mechanism comprises shifting a first threaded surface into engagement with a second threaded surface.

2. The method of claim 1 further comprising releasably coupling the cap member to an elongate drive member, shifting the elongate drive member linearly toward the coupling device without rotation to secure the cap to the coupling device, disengaging the cap member from the drive member, and retracting the drive member away from the coupling device.

3. The method of claim 2, wherein the drive member is first shifted to a provisional lock position where the cap releasably coupled thereto is shifted partway into the coupling device and secured thereto, and subsequently shifted to a full lock position where the cap is shifted fully into the coupling device to immobilize the rod in the coupling device.

4. The method of claim 2, further comprising securing the drive member to the reducing member prior to shifting the drive member linearly.

5. The method of claim 1 wherein applying force to the rod reducing member shifts the spinal rod to a predetermined seated position within the coupling device, and driving the cap member into locking engagement with the coupling device locks the spinal rod in the predetermined seated position.

6. A method for securing a spinal rod to a vertebra, the method comprising:
  securing a fixation device and a coupling device to the vertebra;
  securing a rod reducing assembly to the coupling device so that the spinal rod is positioned between the coupling device and a reducing member of the rod reducing assembly;
  engaging the spinal rod with the reducing member outside and on each side of the coupling device;
  applying force to the reducing member to shift the spinal rod into the coupling device;
  inserting a drive member of a cap inserter into a throughbore of the rod reducing assembly;
  operating an actuator of an actuator assembly of the cap inserter to drive the drive member in an advancing axial direction through the throughbore for advancing a cap member into locking engagement with the coupling device;
  releasably anchoring a coupling portion of the actuator assembly to the rod reducing assembly upon operation of the actuator to restrict relative axial movement between the actuator assembly coupling portion and the rod reducing assembly as the drive member is driven through the throughbore; and
  linearly shifting the reducing member without rotation to contact the spinal rod, engaging the reducing member with a drive mechanism, and then using the drive mechanism to shift the spinal rod into the coupling device.

7. The method of claim 6 further comprising releasably coupling the cap member to the drive member, shifting the drive member linearly toward the coupling device without rotation of the cap member to secure the cap to the coupling device, disengaging the cap member from the drive member, and retracting the drive member away from the coupling device.

8. The method of claim 6 wherein applying force to the rod reducing member shifts the spinal rod to a predetermined seated position within the coupling device, and advancing the cap member into locking engagement with the coupling device locks the spinal rod in the predetermined seated position.

9. A method for securing a spinal rod to a vertebra, the method comprising:
  securing a fixation device and a coupling device to the vertebra;
  securing a rod reducing assembly to the coupling device so that the spinal rod is positioned between the coupling device and a reducing member of the rod reducing assembly;
  engaging the spinal rod with the reducing member outside and on each side of the coupling device;
  applying force to the reducing member to shift the spinal rod into the coupling device;
  inserting a drive member of a cap inserter into a throughbore of the rod reducing assembly;
  operating an actuator of an actuator assembly of the cap inserter to drive the drive member in an advancing axial direction through the throughbore for advancing a cap member into locking engagement with the coupling device; and
  releasably anchoring a coupling portion of the actuator assembly to the rod reducing assembly upon operation of the actuator to restrict relative axial movement between the actuator assembly coupling portion and the rod reducing assembly as the drive member is driven through the throughbore; and
    releasably coupling the cap member to the drive member, shifting the drive member linearly toward the coupling device without rotation of the cap member to secure the cap to the coupling device, disengaging the cap member from the drive member, and retracting the drive member away from the coupling device;
    wherein the drive member is first shifted to a provisional lock position where the cap releasably coupled thereto is shifted partway into the coupling device and secured thereto, and subsequently shifted to a full lock position where the cap is shifted fully into the coupling device to immobilize the rod in the coupling device.

10. A method for securing a spinal rod to a vertebra, the method comprising:
  securing a fixation device and a coupling device to the vertebra;
  securing a rod reducing assembly to the coupling device so that the spinal rod is positioned between the coupling device and a reducing member of the rod reducing assembly;
    disengaging a drive mechanism for the rod reducing member while the rod reducing assembly is secured to the coupling device;
    shifting the reducing member against the spinal rod without operation of the drive mechanism;
    engaging the drive mechanism for driving the reducing member;
  operating the drive mechanism to apply force to the reducing member to shift the spinal rod into the coupling device;
    inserting a drive member of a cap inserter into a throughbore of the rod reducing assembly;
    operating an actuator of an actuator assembly of the cap inserter to drive the drive member in an advancing axial direction through the throughbore for advancing a cap member into locking engagement with the coupling device; and
    releasably anchoring a coupling portion of the actuator assembly to the rod reducing assembly upon operation of the actuator to restrict relative axial movement between the actuator assembly coupling portion and the rod reducing assembly as the drive member is driven through the throughbore.

11. The method of claim 10 wherein applying force to the rod reducing member shifts the spinal rod to a predetermined seated position within the coupling device, and advancing the cap member into locking engagement with the coupling device locks the spinal rod in the predetermined seated position.

12. The method of claim 10 further comprising linearly shifting the reducing member without rotation to contact the spinal rod, engaging the reducing member with a drive mechanism, and then using the drive mechanism to shift the spinal rod into the coupling device.

13. The method of claim 10 further comprising releasably coupling the cap member to the drive member, shifting the drive member linearly toward the coupling device without rotation of the cap member to secure the cap to the coupling device, disengaging the cap member from the drive member, and retracting the drive member away from the coupling device.

14. The method of claim 13, wherein the drive member is first shifted to a provisional lock position where the cap releasably coupled thereto is shifted partway into the coupling device and secured thereto, and subsequently shifted to a full lock position where the cap is shifted fully into the coupling device to immobilize the rod in the coupling device.

15. A method for securing a spinal rod to a vertebra, the method comprising:
 securing a fixation device and a coupling device to the vertebra;
securing a rod reducing assembly to the coupling device so that the spinal rod is positioned between the coupling device and a reducing member of the rod reducing assembly;
 disengaging a drive mechanism for the rod reducing member with the rod reducing assembly secured to the coupling device;
shifting the reducing member into contact with the spinal rod without operation of the drive mechanism;
 engaging the drive mechanism for driving the reducing member;
operating the drive mechanism to apply force to the reducing member to shift the spinal rod into the coupling device; and driving a cap member into locking engagement with the coupling device after the reducing member has shifted the rod into the coupling device;
 wherein the drive mechanism is threaded.

16. The method of claim 15, wherein the step of disengaging the drive mechanism comprises shifting a first set of threads of the drive mechanism away from a second set of threads of the drive mechanism and wherein the step of engaging the drive mechanism comprises shifting the first set of threads of the drive mechanism into engagement with the second set of threads of the drive mechanism.

17. A method for securing a spinal rod to a vertebra, the method comprising:
 securing a fixation device and a coupling device to the vertebra;
securing a rod reducing assembly to the coupling device so that the spinal rod is positioned between the coupling device and a reducing member of the rod reducing assembly;
engaging the spinal rod with the reducing member outside and on each side of the coupling device;
applying force to the reducing member to shift the spinal rod into the coupling device;
inserting a drive member of a cap inserter into a throughbore of the rod reducing assembly;
operating an actuator of an actuator assembly of the cap inserter to drive the drive member in an advancing axial direction through the throughbore for advancing a cap member into locking engagement with the coupling device; and
releasably anchoring a coupling portion of the actuator assembly to the rod reducing assembly upon operation of the actuator to restrict relative axial movement between the actuator assembly coupling portion and the rod reducing assembly as the drive member is driven through the throughbore;
wherein releasably anchoring the cap inserter to the reducing assembly comprises shifting a locking mechanism of the cap inserter into a recess in the reducing assembly.

18. A method for securing a spinal rod to a vertebra, the method comprising:
 securing a fixation device and a coupling device to the vertebra;
 securing a rod reducing assembly to the coupling device so that the spinal rod is positioned between the coupling device and a reducing member of the rod reducing assembly;
 engaging the spinal rod with the reducing member outside and on each side of the coupling device;
 applying force to the reducing member to shift the spinal rod into the coupling device;
 inserting a drive member of a cap inserter into a throughbore of the rod reducing assembly;
 operating an actuator of an actuator assembly of the cap inserter to drive the drive member in an advancing axial direction through the throughbore for advancing a cap member into locking engagement with the coupling device;
 releasably anchoring a coupling portion of the actuator assembly to the rod reducing assembly upon operation of the actuator to restrict relative axial movement between the actuator assembly coupling portion and the rod reducing assembly as the drive member is driven through the throughbore; and
 manipulating a single actuator to releasably anchor the cap inserter member to the reducing assembly and to shift the drive member to advance the cap member.

* * * * *

UNITED STATES PATENT AND TRADEMARK OFFICE
CERTIFICATE OF CORRECTION

| | | |
|---|---|---|
| PATENT NO. | : 8,308,774 B2 | Page 1 of 1 |
| APPLICATION NO. | : 12/031655 | |
| DATED | : November 13, 2012 | |
| INVENTOR(S) | : Jeffrey Hoffman et al. | |

It is certified that error appears in the above-identified patent and that said Letters Patent is hereby corrected as shown below:

On the Title Page

Item (75), under "Inventors", delete "Parrow" and insert -- Perrow --.

Signed and Sealed this
Fifteenth Day of October, 2013

Teresa Stanek Rea
*Deputy Director of the United States Patent and Trademark Office*